US012557981B2

(12) United States Patent
Soares et al.

(10) Patent No.: US 12,557,981 B2
(45) Date of Patent: Feb. 24, 2026

(54) INFORMATION PROCESSING SYSTEM, INFORMATION PROCESSING APPARATUS, INFORMATION PROCESSING PROGRAM, AND INFORMATION PROCESSING METHOD

(71) Applicants: NIKON CORPORATION, Tokyo (JP); Optos plc, Dunfermline Fife (GB)

(72) Inventors: Devin Soares, Marlborough, MA (US); Branden Coleman, Marlborough, MA (US); Bradley Yates, Marlborough, MA (US); Naoyuki Kawachi, Tokyo (JP)

(73) Assignees: NIKON CORPORATION, Tokyo (JP); OPTOS PLC, Dunfermline Fife (GB)

( * ) Notice: Subject to any disclaimer, the term of this patent is extended or adjusted under 35 U.S.C. 154(b) by 928 days.

(21) Appl. No.: 17/631,242

(22) PCT Filed: Jul. 29, 2020

(86) PCT No.: PCT/JP2020/029058
§ 371 (c)(1),
(2) Date: Jan. 28, 2022

(87) PCT Pub. No.: WO2021/020444
PCT Pub. Date: Feb. 4, 2021

(65) Prior Publication Data
US 2022/0280034 A1 Sep. 8, 2022

Related U.S. Application Data

(60) Provisional application No. 62/880,975, filed on Jul. 31, 2019.

(51) Int. Cl.
*A61B 3/00* (2006.01)
*G06V 40/18* (2022.01)
(Continued)

(52) U.S. Cl.
CPC .......... *A61B 3/0025* (2013.01); *G06V 40/193* (2022.01); *G16H 30/20* (2018.01); *G16H 50/20* (2018.01)

(58) Field of Classification Search
CPC .... A61B 3/0025; G06V 40/193; G16H 30/20; G16H 50/20; G16H 10/60; G16H 40/63; G16H 40/67; G16H 30/40
(Continued)

(56) References Cited

U.S. PATENT DOCUMENTS

| | | |
|---|---|---|
| 2017/0156582 A1 | 6/2017 | Ehlers et al. |
| 2019/0221313 A1 | 7/2019 | Rim et al. |
| 2020/0085290 A1 | 3/2020 | Wang et al. |

FOREIGN PATENT DOCUMENTS

| | | |
|---|---|---|
| JP | H11-338950 A | 12/1999 |
| JP | 2004-070562 A | 3/2004 |

(Continued)

OTHER PUBLICATIONS

International Search Report with English translation and Written Opinion issued in corresponding application No. PCT/JP2020/059058 dated Oct. 27, 2020.

(Continued)

*Primary Examiner* — Bumsuk Won
*Assistant Examiner* — Rahman Abdur
(74) *Attorney, Agent, or Firm* — Foley & Lardner LLP

(57) ABSTRACT

An information processing apparatus that is communicably connected with another information processing apparatus, the information processing apparatus comprises: a processor configured to execute a program; and a storage device configured to store the program, the processor being configured to execute: acquisition processing of acquiring agreement information relating to the usage of subject eye image data of a patient by the other information processing (Continued)

apparatus; and transmission processing of transmitting the subject eye image data to the other information processing apparatus on the basis of the agreement information acquired by the acquisition processing.

15 Claims, 16 Drawing Sheets

(51) Int. Cl.
  *G16H 30/20*         (2018.01)
  *G16H 50/20*         (2018.01)

(58) Field of Classification Search
  USPC ......................................................... 351/206
  See application file for complete search history.

(56)                References Cited

FOREIGN PATENT DOCUMENTS

| | | | |
|---|---|---|---|
| JP | 2006-201830 | A | 8/2006 |
| JP | 2008-204378 | A | 9/2008 |
| JP | 2015-221276 | A | 12/2015 |
| JP | 5951086 | B2 | 7/2016 |
| JP | 2018-013826 | A | 1/2018 |
| JP | 2018-106402 | A | 7/2018 |
| JP | 2018-121885 | A | 8/2018 |
| WO | WO-2014/157729 | A1 | 10/2014 |
| WO | WO-2018/201632 | A1 | 11/2018 |

OTHER PUBLICATIONS

Extended European Search Report issued in corresponding European Patent Application No. 20845931.3, dated Aug. 1, 2023 (11 pages).

INFORMATION PROCESSING SYSTEM, INFORMATION PROCESSING APPARATUS, INFORMATION PROCESSING PROGRAM, AND INFORMATION PROCESSING METHOD

CROSS-REFERENCE TO RELATED APPLICATIONS

The present application is a national stage entry of PCT/JP2020/029058, filed on Jul. 29, 2020, which claims priority from U.S. provisional application 62/880,975 filed on Jul. 31, 2019, the contents of all of which are hereby incorporated by reference in their entirety.

BACKGROUND

The present invention relates to an information processing system, an information processing apparatus, an information processing program, and an information processing method.

An ophthalmologic information processing server is known (JP2015-221276 A). The ophthalmologic information processing server can analyze a variety of types of ophthalmologic images. However, handling of information indicating agreement by a patient is not considered.

SUMMARY

First disclosure of an information processing system is an information processing system including an image acquisition apparatus configured to acquire subject eye image data of a patient, a first information processing apparatus which is communicably connected with the image acquisition apparatus and stores the subject eye image data, and a second information processing apparatus which is communicably connected with the first information processing apparatus and performs image diagnosis using the subject eye image data, wherein the image acquisition apparatus is configured to execute: first generation processing of generating first agreement information indicating permission or non-permission for transmitting the subject eye image data to the first information processing apparatus, and second agreement information indicating permission or non-permission for reusing the subject eye image data by the second information processing apparatus for after image diagnosis with the second information processing apparatus; and first transmission processing of, when the first agreement information indicates transmission permission, transmitting first transmission data including patient information of the patient, the subject eye image data and the second agreement information to the first information processing apparatus, wherein the first information processing apparatus is configured to execute: storage processing of storing the subject eye image data when the first transmission data is received from the image acquisition apparatus; second generation processing of generating identification information unique to the subject eye image data when the first transmission data is received; and second transmission processing of transmitting second transmission data including the identification information, the subject eye image data, and the second agreement information to the second information processing apparatus, wherein the second information processing apparatus is configured to execute: image diagnosis processing of executing image diagnosis on the basis of the subject eye image data when the second transmission data is received from the first information processing apparatus; data processing of deleting the subject eye image data after the image diagnosis processing when the second agreement information indicates non-permission for reusing the subject eye image data, and storing the subject eye image data and an image diagnosis result of the image diagnosis processing in a database when the second agreement information indicates permission for reuse of the subject eye image data; and third transmission processing of transmitting third transmission data including the identification information and the image diagnosis result to the first information processing apparatus.

Second disclosure of an information processing system is an information processing system that is communicably connected with a first information processing apparatus which stores subject eye image data of a patient and a second information processing apparatus which is communicably connected with the first information processing apparatus, wherein the first information processing apparatus is configured to execute first transmission processing of transmitting the subject eye image data to the second information processing apparatus on the basis of agreement information relating to agreement to use of the subject eye image data of the patient by the second information processing apparatus, wherein the second information processing apparatus is configured to execute: image diagnosis processing of executing image diagnosis on the basis of the subject eye image transmitted by the first transmission processing, and second transmission processing of transmitting image diagnosis results obtained by the image diagnosis processing to the first information processing apparatus.

Third disclosure of an information processing apparatus is an information processing apparatus that is communicably connected with another information processing apparatus, the information processing apparatus comprising: a processor configured to execute a program; and a storage device configured to store the program, the processor being configured to execute: acquisition processing of acquiring agreement information relating to the usage of subject eye image data of a patient by the other information processing apparatus; and transmission processing of transmitting the subject eye image data to the other information processing apparatus on the basis of the agreement information acquired by the acquisition processing.

Fourth disclosure of an information processing apparatus is an information processing apparatus that is communicably connected with another information processing apparatus which stores subject eye image data of a patient, the information processing apparatus comprising: a processor configured to execute a program; and a storage device configured to store the program, the information processing apparatus able to access a database which stores learning data, the processor being configured to execute: reception processing of receiving, from the another information processing apparatus, the subject eye image data and non-permission or agreement information for reuse of the subject eye image data by the information processing apparatus; image diagnosis processing of performing image diagnosis on the basis of the subject eye image data received by the reception processing; transmission processing of transmitting an image diagnosis result obtained by the image diagnosis processing to the other information processing apparatus; and data control processing of controlling to delete the subject eye image data or store the subject eye image data in the database on the basis of the non-permission or agreement information received by the reception processing.

Fifth disclosure of an information processing apparatus is an information processing apparatus that is communicably connected with another first information processing apparatus which stores subject eye image data of a patient and another second information processing apparatus including a database which stores learning data, the information processing apparatus comprising: a processor configured to execute a program; and a storage device configured to store the program, the processor being configured to execute: reception processing of receiving, from the first information processing apparatus, the subject eye image data and non-permission or agreement information for reuse of the subject eye image data by the information processing apparatus; image diagnosis processing of performing image diagnosis on the basis of the subject eye image data received by the reception processing; transmission processing of transmitting an image diagnosis result obtained by the image diagnosis processing to the other first information processing apparatus; and data processing of deleting the subject eye image data or transmitting the subject eye image data to the other second information processing apparatus on the basis of the non-permission or agreement information received by the reception processing.

Sixth disclosure of an information processing program which causes a processor in an information processing apparatus that is communicably connected with another information processing apparatus to execute: acquisition processing of acquiring agreement information relating to agreement of usage of subject eye image data of a patient by the other information processing apparatus; and transmission processing of transmitting the subject eye image data to the other information processing apparatus on the basis of the agreement information acquired by the acquisition processing.

Seventh disclosure of an information processing program which causes a processor in an information processing apparatus that is communicably connected with another information processing apparatus which stores subject eye image data of a patient, and access a database storing learning data to execute: reception processing of receiving, from the another information processing apparatus, the subject eye image data and non-permission or agreement information for reuse of the subject eye image data by the information processing apparatus; image diagnosis processing of performing image diagnosis on the basis of the subject eye image data received by the reception processing; transmission processing of transmitting an image diagnosis result obtained by the image diagnosis processing to the other information processing apparatus; and data control processing of controlling to delete the subject eye image data or store the subject eye image data in the database on the basis of the non-permission or agreement information received by the reception processing.

Eighth disclosure of an information processing program for causing a processor in an information processing apparatus that is communicably connected with another first information processing apparatus which stores subject eye image data of a patient and another second information processing apparatus including a database which stores learning data to execute: reception processing of receiving, from the first information processing apparatus, the subject eye image data and permission or non-agreement information for reuse of the subject eye image data by the information processing apparatus; image diagnosis processing for performing image diagnosis on the basis of the subject eye image data received by the reception processing; transmission processing of transmitting an image diagnosis result obtained by the image diagnosis processing to the other information processing apparatus; and data control processing of controlling to delete the subject eye image data or store the subject eye image data in the database on the basis of the non-permission or agreement information received by the reception processing.

Ninth disclosure of an information processing method is an information processing method executed by an information processing apparatus that is communicably connected with another information processing apparatus and comprises a processor configured to execute a program; and a storage device configured to store the program executed by the processor, the information processing method comprising: acquisition processing of acquiring agreement information relating to the usage of subject eye image data of a patient by the other information processing apparatus; and transmission processing of transmitting the subject eye image data to the other information processing apparatus on the basis of the agreement information acquired by the acquisition processing.

Tenth disclosure of an information processing method is an information processing method executed by an information processing apparatus that is communicably connected with another information processing apparatus which stores subject eye image data of a patient, and is able to access a database which stores learning data, the information processing method comprising: reception processing of receiving, from the another information processing apparatus, the subject eye image data and non-permission or agreement information for reuse of the subject eye image data by the information processing apparatus; image diagnosis processing of performing image diagnosis on the basis of the subject eye image data received by the reception processing; transmission processing of transmitting an image diagnosis result obtained by the image diagnosis processing to the other information processing apparatus; and data control processing of controlling to delete the subject eye image data or store the subject eye image data in the database on the basis of the non-permission or agreement information received by the reception processing.

Eleventh disclosure of an information processing method is an information processing method executed by an information processing apparatus that is communicably connected with another first information processing apparatus which stores subject eye image data of a patient and another second information processing apparatus including a database which stores learning data, the information processing method comprising: reception processing of receiving, from the first information processing apparatus, the subject eye image data and non-permission or agreement information for reuse of the subject eye image data by the information processing apparatus; image diagnosis processing of performing image diagnosis on the basis of the subject eye image data received by the reception processing; transmission processing of transmitting an image diagnosis result obtained by the image diagnosis processing to the other first information processing apparatus; and data processing of deleting the subject eye image data or transmitting the subject eye image data to the other second information processing apparatus on the basis of the non-permission or agreement information received by the reception processing.

DETAILED DESCRIPTION OF THE EMBODIMENT

First Embodiment

Example of Image Diagnosis Using Agreement Information

Figure 1:
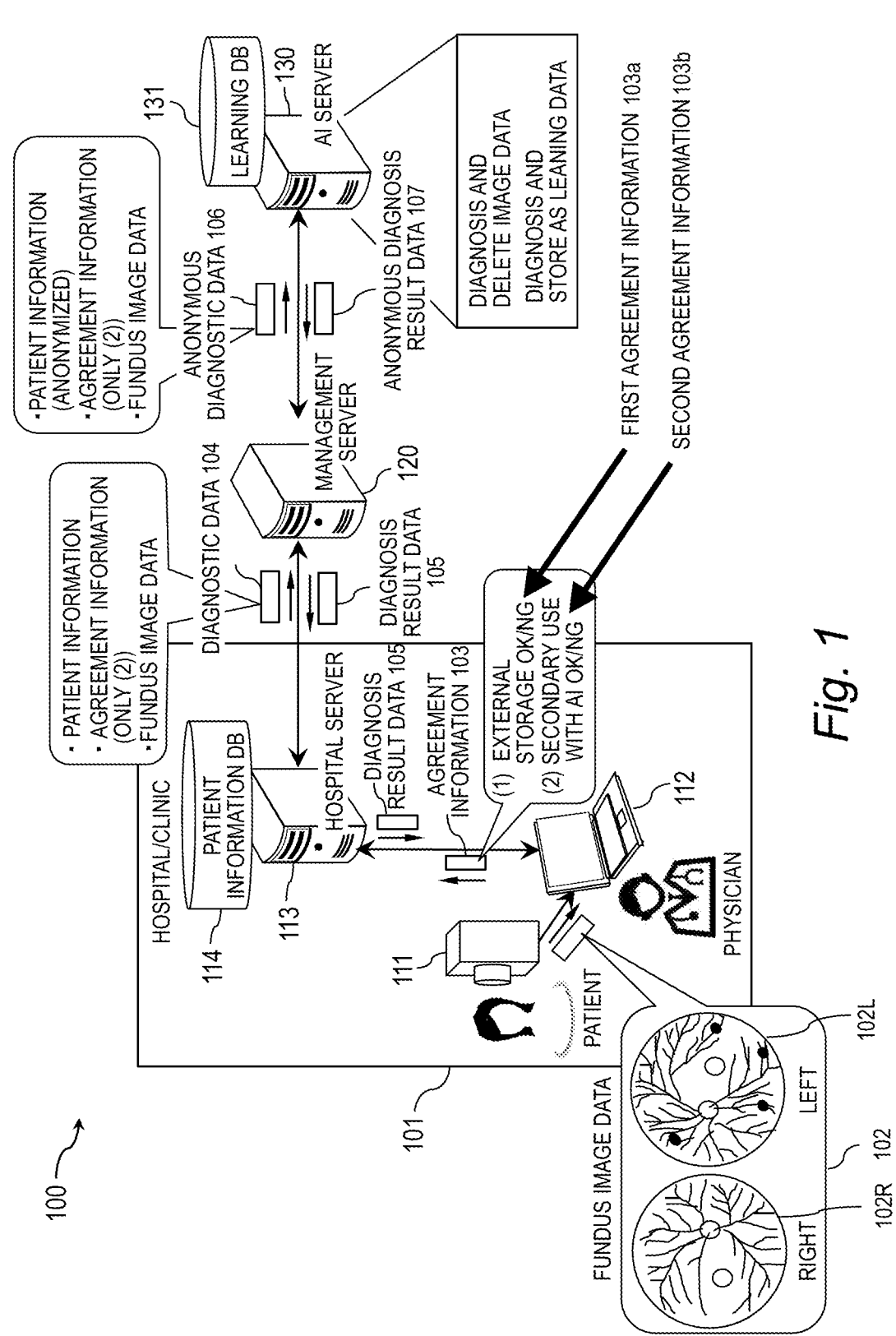
FIG. 1 is a diagram illustrating an example of fundus image diagnosis using agreement information.

FIG. 1 is a diagram illustrating an example of fundus image diagnosis using agreement information. The fundus image diagnosis using agreement information is executed by an information processing system 100. The information processing system 100 includes a hospital system 101, a management server 120, and an artificial intelligence (AI) server 130. The hospital system 101 and the management server 120 are communicably connected to each other. The management server 120 and the AI server 130 are communicably connected to each other.

The hospital system 101 is provided in, for example, a hospital or a clinic (ophthalmological clinic, internal medicine clinic, diabetes clinic, etc.). The hospital system 101 includes an ophthalmological device 111, a terminal 112, and a hospital server 113. The ophthalmological device 111 is communicably connected to the terminal 112. The ophthalmological device 111 is a fundus camera or a device such as a scanning laser ophthalmoscope or an optical coherence tomography machine that scans a subject eye with laser light to generate an image based on light reflected from the fundus. The ophthalmological device 111 generates fundus image data 102R, 102L of a subject eye. When not distinguishing between the fundus image data 102R for the right eye and the fundus image data 102L for the left eye, the fundus image data is referred to as "fundus image data 102". The same applies to other components with reference symbols ending in "R" and "L". The ophthalmological device 111 transmits the generated fundus image data 102 to the terminal 112. The fundus image data 102 includes the shooting date.

The fundus image data may be any one of fundus image data shot by a fundus camera, fundus image data of a fundus shot by a scanning laser ophthalmoscope, or tomographic data of a fundus shot by an optical coherence tomography machine. Alternatively, the fundus image data may be a fundus image dataset consisted of a combination of two or more of the above-described types of data.

The ophthalmological device 111 includes at least one of, for example, a fundus camera, a scanning laser ophthalmoscope, and an optical coherence tomography machine. Thus, the fundus image data 102 is one of or a combination of two or more of fundus image data shot by a fundus camera, fundus image data shot by a scanning laser ophthalmoscope, or tomographic data of a fundus shot by an optical coherence tomography machine.

The terminal 112 is a computer capable of communicating with the ophthalmological device 111 and the hospital server 113. The terminal 112 may be configured to directly communicate with the management server 120. The terminal 112 is used by a physician, for example. The terminal 112 is, for example, a personal computer or a tablet. The terminal 112 forwards the fundus image data 102 from the ophthalmological device 111 to the hospital server 113.

Further, the terminal 112 transmits an agreement information 103 to the hospital server 113. The agreement information 103 is information indicating whether a patient i agrees with usage of the fundus image data 102 of the patient's subject eye outside of the hospital system 101. Specifically, the agreement information 103 includes, for example, a first agreement information 103a and a second agreement information 103b.

The first agreement information 103a is, for example, an external storage flag indicating permission or non-permission for transmitting the fundus image data 102 to the management server 120 outside of the hospital system 101. If the external storage flag is "1", this indicates permission (OK) for transmitting the fundus image data 102 to the management server 120 outside of the hospital system 101. If the external storage flag is "0", this indicates non-permission (NG) for transmitting the fundus image data 102 to the management server 120 outside of the hospital system 101.

The second agreement information 103b is, for example, a secondary use flag indicating permission or non-permission for reuse of the fundus image data 102 in an AI server 130 outside of the hospital system 101. If the secondary use flag is "1", this indicates permission (OK) for reusing the fundus image data 102 in the AI server 130. If the secondary use flag is "0", this indicates non-permission (NG) for reusing the fundus image data 102 in the AI server 130. The agreement information 103 exists for each patient i. The agreement information 103 may have an expiration date. Further, separate agreement information 103 may exist for each patient i each time the image data is shot. The agreement information 103 may have any data format provided that the hospital server 113, the management server 120, and the AI server 130 can recognize the agreement information 103.

The terminal 112 receives patient information and diagnosis result data 105 from the hospital server 113 and displays the patient information and the diagnosis result data 105 on a display screen. The fundus image data 102 from the ophthalmological device 111, the patient information from the hospital server 113, the diagnosis result included in the diagnosis result data 105 and the agreement information 103 are associated with the same ID (for example, a patient ID) by the terminal 112 or the hospital server 113.

The hospital server 113 is a computer that can communicate with the terminal 112 and the management server 120. The hospital server 113 includes a patient information DB 114. The patient information DB 114 is a database that stores patient information. The hospital server 113 receives a patient ID and the fundus image data 102 from the terminal 112. The hospital server 113 stores the fundus image data 102, the diagnosis result included in the diagnosis result data, and the agreement information 103 in the patient information DB 114 in association with the patient information identified by the patient ID.

When the first agreement information 103a indicates permission for transmitting the fundus image data 102 to the management server 120 outside the hospital system 101, the hospital server 113 transmits a diagnostic data 104 to the management server 120. When the first agreement information 103a indicates non-permission, the hospital server 113 does not transmit the diagnostic data 104. Thus, the hospital server 113 can protect the first agreement information 103a related to the patient i. The diagnostic data 104 includes the patient information related to the patient i, the fundus image data 102, and the second agreement information 103b. The hospital server 113 receives the diagnosis result data 105 from the management server 120. The hospital server 113 stores the diagnosis result included in the received diagnosis result data 105 in the patient information DB 114.

The management server 120 is a computer that can communicate with the hospital server 113 and the AI server 130. The management server 120 receives the diagnostic data 104 from the hospital server 113. The management server 120 anonymizes the received diagnostic data 104. Specifically, for example, the management server 120 issues a new ID (hereinafter, "anonymization ID") and associates that ID with the patient information in the received diagnostic data 104. Then, the management server 120 handles a combination of the anonymization ID and the fundus image data 102 as an anonymous diagnostic data 106.

The patient ID in the patient information may be used as the anonymization ID. In this case, the anonymous diagnostic data 106 is made up of the patient ID as the anonymization ID, the fundus image data 102, and the second agreement information 103b. Thus, the patient information is anonymized. Note that the management server 120 may store any information not uniquely identifying the patient i among the patient information in the anonymous diagnostic data 106. The information not uniquely identifying the patient i is, for example, the eyesight, sex, age or nationality of the patient i.

Further, the management server 120 may encrypt the patient information. In this case, the management server 120 transmits a combination of the encrypted patient information and the fundus image data 102 to the AI server 130 as anonymous diagnostic data.

The management server 120 receives an anonymous diagnosis result data 107 from the AI server 130. The anonymous diagnosis result data 107 includes the anonymization ID in the anonymous diagnostic data 106 and a diagnosis result indicating the severity (also referred to as progression) of a disease in the subject eye. The management server 120 converts the received anonymous diagnosis result data 107 into the diagnosis result data 105.

Specifically, for example, the management server 120 acquires patient information associated with the anonymization ID included in the received anonymous diagnosis result data 107 and replaces the patient information with patient information acquired from the anonymization ID, to thereby generate the diagnosis result data 105 including patient information and a diagnosis result.

When the management server 120 transmits the anonymous diagnostic data 106, which is a combination of the encrypted patient information, the fundus image data 102, and the second agreement information 103b, to the AI server 130, the management server 120 receives the anonymous diagnosis result data 107 including the encrypted patient information and the diagnosis result from the AI server 130.

In this case, the management server 120 decrypts the encrypted patient information to convert the anonymous diagnosis result data 107 into the diagnosis result data 105. Thus, the management server 120 can conceal patient information through anonymization and encryption and protect personal information. Then, the management server 120 transmits the generated diagnosis result data 105 to the hospital server 113.

The AI server 130 is a computer that conducts fundus image diagnosis by AI using learning parameters obtained by machine learning and deep learning. The AI server 130 learns a combination of past fundus image data 103 and the progression of that data as training data to generate learning parameters. The training dataset and the learning parameters are stored in a learning DB 131. The learning DB 131 stores findings 105 related to progression. These learning parameters are used to extract features from a fundus image using a computer neural network (CNN). Then, symptoms in the input fundus image are estimated based on the features.

The AI server 130 receives the anonymous diagnostic data 106. The AI server 130 inputs the fundus image data 102 included in the anonymous diagnostic data 106 to the learning model in which the learning parameters are applied to the CNN and outputs a severity.

The AI server 130 generates the anonymous diagnosis result data 107 including the anonymization ID included in the anonymous diagnostic data 106 and the degree of severity output from the learning model. The AI server 130 transmits the generated anonymous diagnosis result data 107 to the management server 120.

When the second agreement information 103 indicates permission for reuse of the fundus image data in the AI server 130 after image diagnosis is conducted on the AI server 130 outside the hospital system 101, the AI server 130 adds a combination of the severity and the fundus image data 102, which is the output source of the severity, to a learning dataset in a learning DB as learning data. When the second agreement information 103 indicates non-permission, the AI server 130 does not add to the learning dataset. With this configuration, the AI server 130 can protect the second agreement information 103 of the patient i. Thus, the information processing system 100 can protect the personal information of the patient i.

Hardware Configuration Example of a Computer

Figure 2:
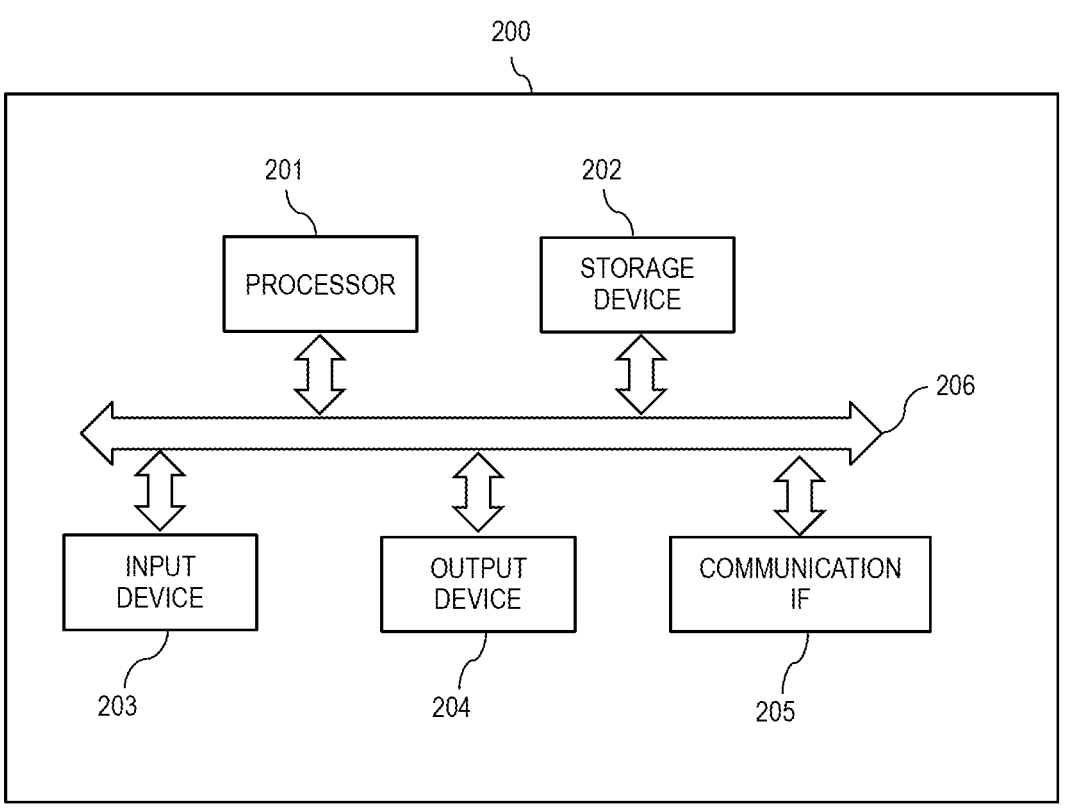
FIG. 2 is a block diagram illustrating a hardware configuration example of a computer.

FIG. 2 is a block diagram illustrating a hardware configuration example of a computer 200 (the terminal 112, the hospital server 113, the management server 120, the AI server 130, a DB server 1400). The computer 200 includes a processor 201, a storage device 202, an input device 203, an output device 204, and a communication interface (communication IF) 205. The processor 201, the storage device 202, the input device 203, the output device 204, and the communication IF 205 are connected to one another by a bus 206. The processor 201 controls the computer 200. The processor 201 executes various programs. The storage device 202 serves as a work area of the processor 201. The storage device 202 is a non-transitory or temporary recording medium which stores the various programs and data. The storage device 202 can be, for example, a read-only memory (ROM), a random-access memory (RAM), a hard disk drive (HDD), or a flash memory. The input device 203 inputs data. The input device 203 can be, for example, a keyboard, a mouse, a touch panel, a ten-key pad, or a scanner. The output device 204 outputs data. The output device 204 can be, for example, a display, a printer or a speaker. The communication IF 205 couples to a network to transmit and receive data.

Patient Information DB 114

Figure 3:
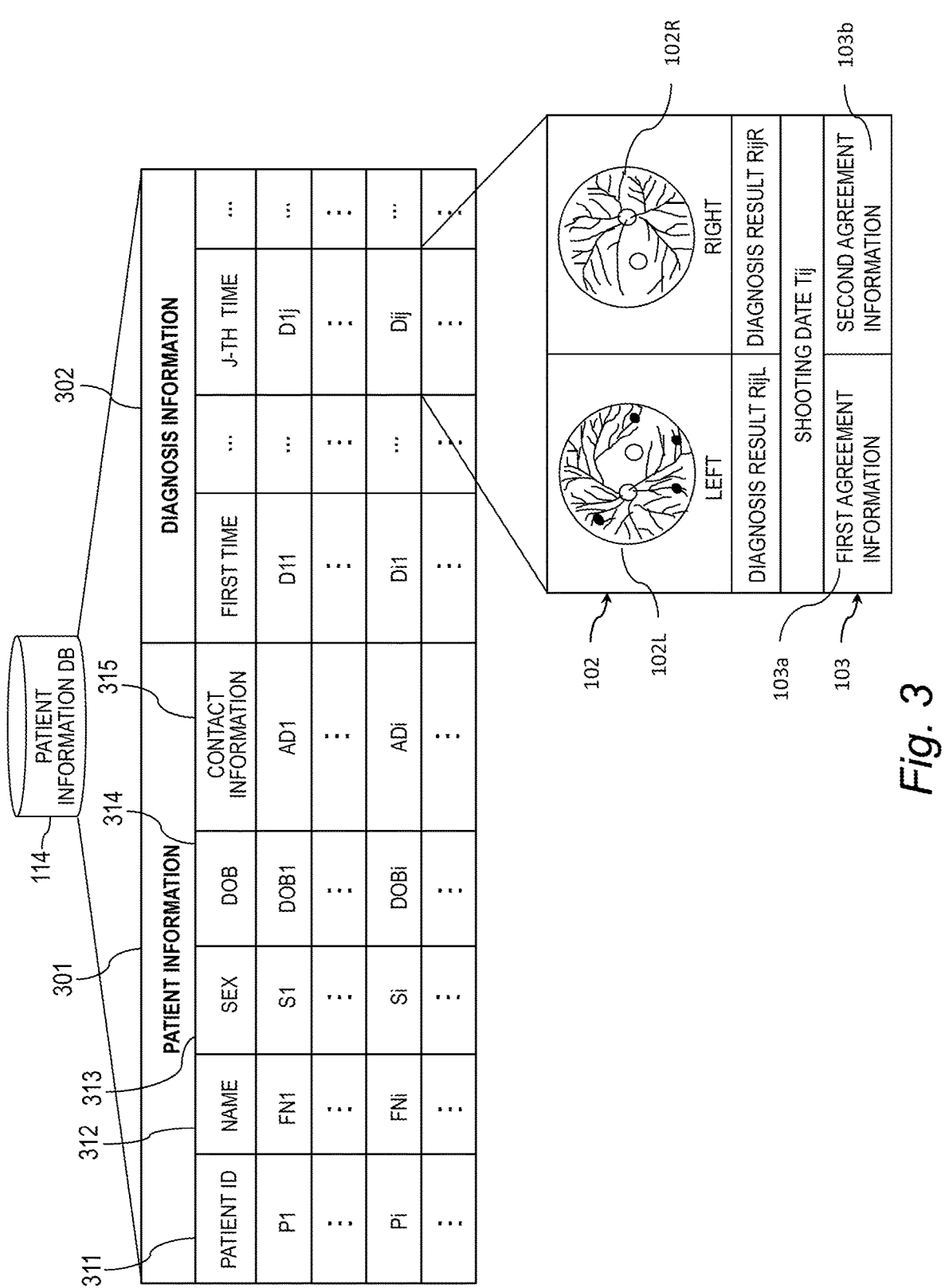
FIG. 3 is a diagram illustrating an example of content stored in the patient information DB.

FIG. 3 is a diagram illustrating an example of content stored in the patient information DB 114. The patient information DB 114 includes a patient information field 301 and a diagnosis information field 302. The patient information field 301 includes, as sub-fields, a patient ID field 311, a name field 312, a sex field 313, a date of birth field 314, and a contact information field 315. The sub-fields 311 to 315 on the same row correspond to patient information related to the patient i (where i is, for example an integer of 1 or more).

The patient ID field 311 is a storage region for storing the patient ID. A patient IDPi is identification information that uniquely identifies the patient i. The name field 312 is a storage region for storing a name FNi of the patient i. The sex field 313 is a storage region for storing a sex Si of the patient i. The date of birth field 314 is a storage region for storing a date of birth DOBi of the patient i. The contact information field 315 is a storage region for storing contact information ADi of the patient i.

The diagnosis information field 302 is a storage region for storing diagnosis information Di1 to Dij until a j-th diagnosis (where j is an integer of 1 or more) of the patient i. The diagnosis information Dij includes the fundus image data 102, a diagnosis result Rij, a shooting date Tij, and the agreement information 103. The diagnosis result Rij includes the severity from the AI server 130. The shooting date Tij is the date on which the fundus image data 102 was generated by imaging an eye with the ophthalmological device 111. The agreement information 103 includes the above-described first agreement information 103*a* (external storage flag) and the second agreement information 103*b* (secondary use flag).

Example of Operation Sequence of Information Processing System 100

Figure 4:
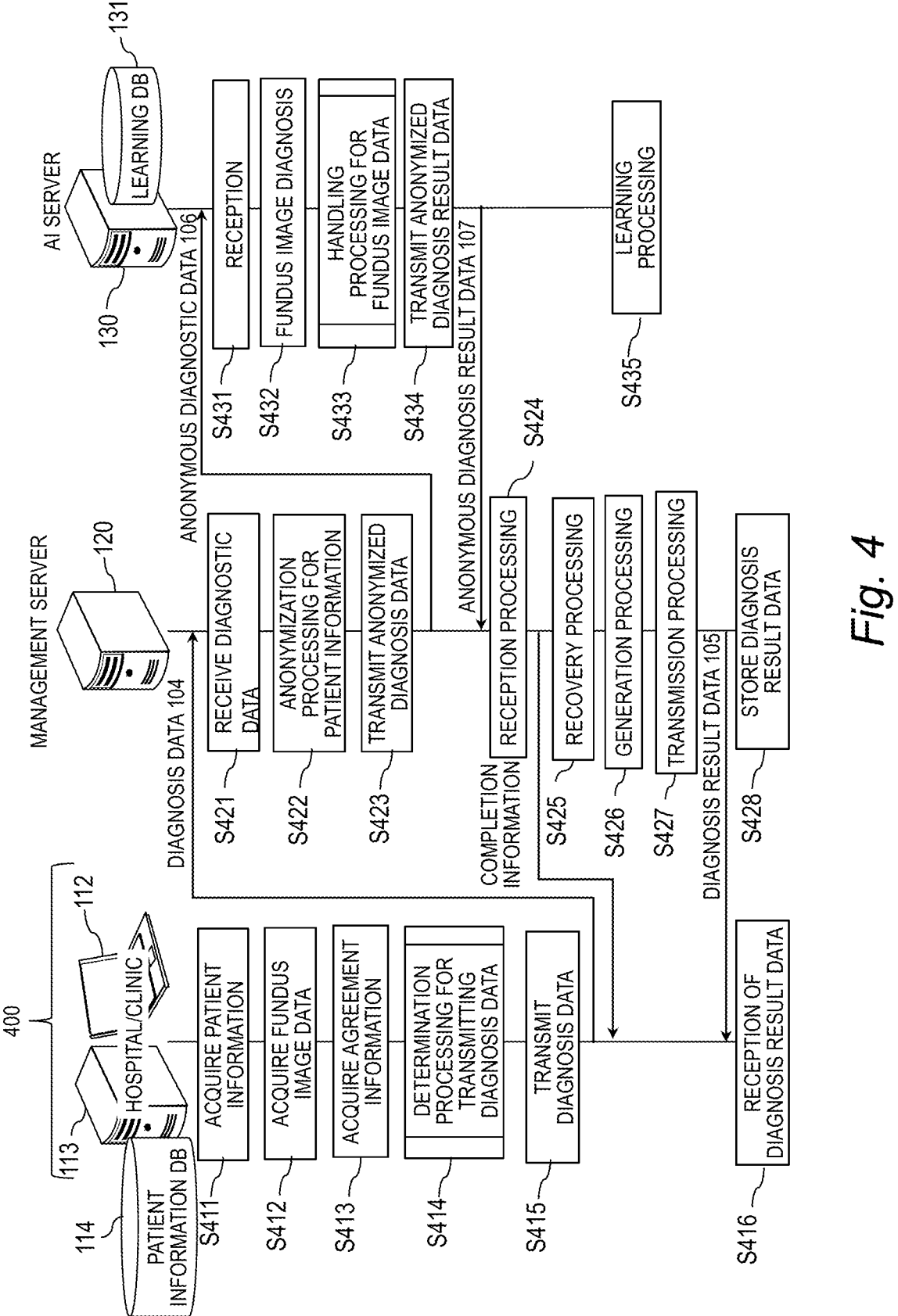
FIG. 4 is a diagram illustrating an example of an operation sequence of the information processing system according to the first embodiment.

FIG. 4 is a diagram illustrating an example of an operation sequence of the information processing system 100 according to the first embodiment. The terminal 112 and the hospital server 113 are collectively referred to as an "image acquisition apparatus 400" when not distinguishing between the two. The image acquisition apparatus 400 acquires, from the patient information DB 114 (Step S411), patient information related to the patient i, who is to be diagnosed. The image acquisition apparatus 400 acquires the fundus image data 102 of the patient i via the terminal 112 (Step S412). The hospital server 113 acquires the agreement information 103 of the patient i via the terminal 112 (Step S413).

Then, the image acquisition apparatus 400 performs determination processing for transmitting for the diagnostic data 104, which includes the patient information acquired in Step S411, the fundus image data 102 acquired in Step S412, and the second agreement information 103*b* acquired in Step S413. The determination processing for transmitting the diagnostic data 104 (Step S414) is processing for determining whether to transmit the diagnostic data 104 depending on the content of the first agreement information 103*a*.

When the first agreement information 103*a* indicates permission for transmitting, the image acquisition apparatus 400 decides to transmit the diagnostic data 104. When the first agreement information 103*a* indicates non-permission for transmitting, the agreement information 103*a* decides to not transmit the diagnostic data 104. Details of the determination processing for transmitting the diagnostic data 104 (Step S414) will be described later. With this configuration, the image acquisition apparatus 400 transmits the diagnostic data 104 only when the image acquisition apparatus 400 decides to transmit the diagnostic data 104 in Step S414 (Step S415).

When the diagnostic data 104 is transmitted from the image acquisition apparatus 400, the management server 120 receives the diagnostic data 104 (Step S421). Next, the management server 120 anonymizes the patient information in the diagnostic data 104 (Step S422). Then, the management server 120 transmits the anonymous diagnostic data 106 including the anonymization ID associated with the patient information, the fundus image data 102, and the second agreement information 103*b* (secondary use flag) to the AI server 130 (Step S423).

When the anonymous diagnostic data 106 is transmitted from the management server 120, the AI server 130 receives the anonymous diagnostic data 106 (Step S431). Next, the AI server 130 inputs the fundus image data 102 included in the anonymous diagnostic data 106 to the learning model to conduct a fundus image diagnosis (Step S432).

After the fundus image diagnosis (Step S432), the AI server 130 performs handling processing for the fundus image data 102 (Step S433). The handling processing for the fundus image data 102 (Step S433) is processing for deciding how to handle the fundus image data 102 subject to fundus image diagnosis (Step S432), for example, using the fundus image data 102 as learning data, on the basis of the content of the second agreement information 103*b*. Details of the handling processing (Step S433) for the fundus image data 102 will be described later.

Then, the AI server 130 transmits, to the management server 120, the anonymous diagnosis result data 107 including the anonymization ID and the diagnosis result Rij indicating the severity output by the fundus image diagnosis (Step S434).

Then, the AI server 130 performs learning processing (Step S435). Specifically, for example, in the handling processing (Step S433) for the fundus image data 102, the AI server 130 adds a combination of the fundus image data 102 included in the anonymous diagnostic data received in Step S431 and the severity, which is the diagnosis result Rij output in Step S432 to the learning dataset in the learning DB 131 and updates the learning model with the added learning dataset only in a case where the combination is permitted to be handled as learning data (the second agreement information 103b (secondary use flag) indicates that secondary use is OK).

When the anonymous diagnosis result data 107 is transmitted from the AI server 130, the management server 120 receives the anonymous diagnosis result data 107 (Step S424). At this time, the management server 120 may transmit completion information indicating that reception of the anonymous diagnosis result data 107 is complete to the image acquisition apparatus 400. Then, the management server 120 recovers the patient information based on the anonymization ID included in the anonymous diagnosis result data 107 (Step S425).

For example, the management server 120 reads out the patient information including the patient ID associated with the anonymization ID held in Step S422. Then, the management server 120 generates the diagnosis result data 105 including that acquired patient information and the diagnosis result Rij (Step S426) and transmits the diagnosis result data 105 to the image acquisition apparatus 400 (Step S427).

When the completion information is received from the management server 120, the image acquisition apparatus 400 may transmit an acquisition request for the diagnosis result data 105 to the management server 120. With this configuration, when the acquisition request is received, the management server 120 transmits the diagnosis result data 105 to the image acquisition apparatus 400. Then, the management server 120 stores the diagnosis result data 105 (Step S428). Then, the processing of the management server 120 ends.

When the diagnosis result data 105 is transmitted from the management server 120, the image acquisition apparatus 400 receives the diagnosis result data 105 (Step S416). With this configuration, the terminal 112 can use the diagnosis result data 105 and the fundus image data 102 from the hospital server 113 to display the fundus image data 102, the severity and the patient information on the display screen. Then, an end button (not shown) is operated by a user and the display processing is ended.

Figure 5:
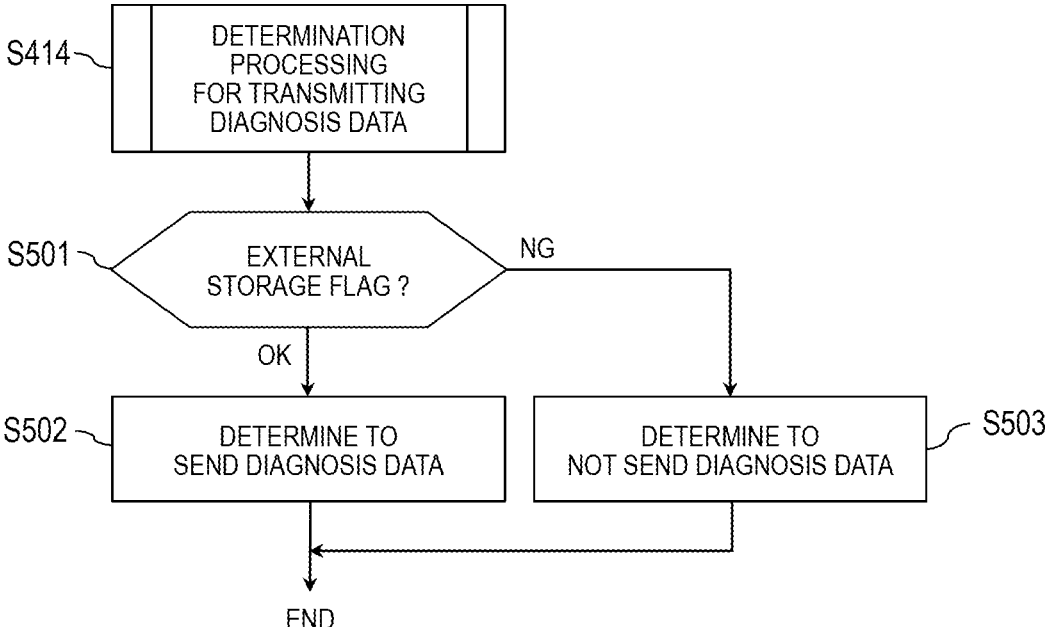
FIG. 5 is a flowchart illustrating a detailed example of a processing procedure of the determination processing for transmitting the diagnostic data (Step S414) illustrated in FIG. 4.

FIG. 5 is a flowchart illustrating a detailed example of a processing procedure of the determination processing for transmitting the diagnostic data 104 (Step S414) illustrated in FIG. 4. When the external storage flag, which is the first agreement information 103a, is "1" indicating permission (OK) for external storage (Step S501: Yes), the image acquisition apparatus 400 decides that the diagnostic data 104 is to be transmitted and ends the determination processing for transmitting the diagnostic data 104 (Step S414). When the external storage flag, which is the first agreement information 103a, is "0" indicating non-permission (NG) for external storage (Step S501: No), the hospital server 113 decides that the diagnostic data 104 is not to be transmitted and ends the determination processing for transmitting the diagnostic data 104 (Step S414). In other words, when the external storage flag, which is the first agreement information 103a, is non-permission (NG) for external storage, only the shot fundus image is stored in the hospital server and image diagnosis using AI is not performed.

Figure 6:
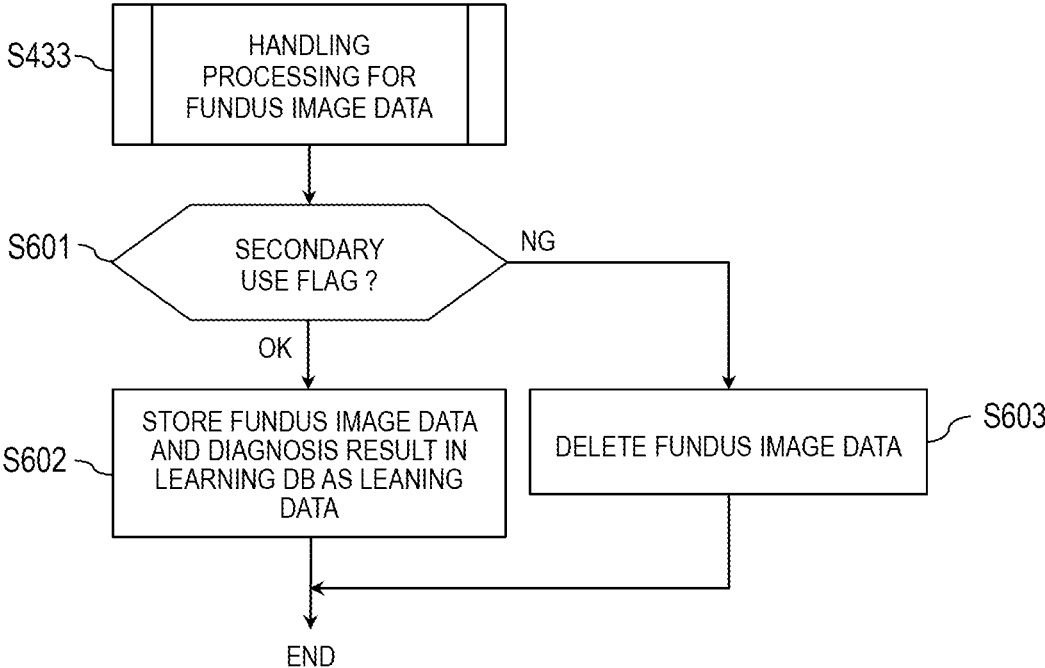
FIG. 6 is a flowchart illustrating a detailed example of a first processing procedure of the handling processing (Step S433) for the fundus image data illustrated in FIG. 4.

FIG. 6 is a flowchart illustrating a detailed example of a first processing procedure of the handling processing (Step S433) for the fundus image data 102 illustrated in FIG. 4. When the secondary use flag, which is the second agreement information 103b, is "1" indicating permission (OK) for secondary use (Step S601: Yes), the AI server 130 stores a combination of the fundus image data 102 and the diagnosis result Rij in the learning DB 131 as learning data and ends the handling processing (Step S433) for the fundus image data 102. When the secondary use flag, which is the second agreement information 103b, is "0" indicating non-permission (NG) for secondary use (Step S601: No), the AI server 130 deletes the fundus image data 102 and ends the handling processing (Step S433) for the fundus image data 102.

Figure 7:
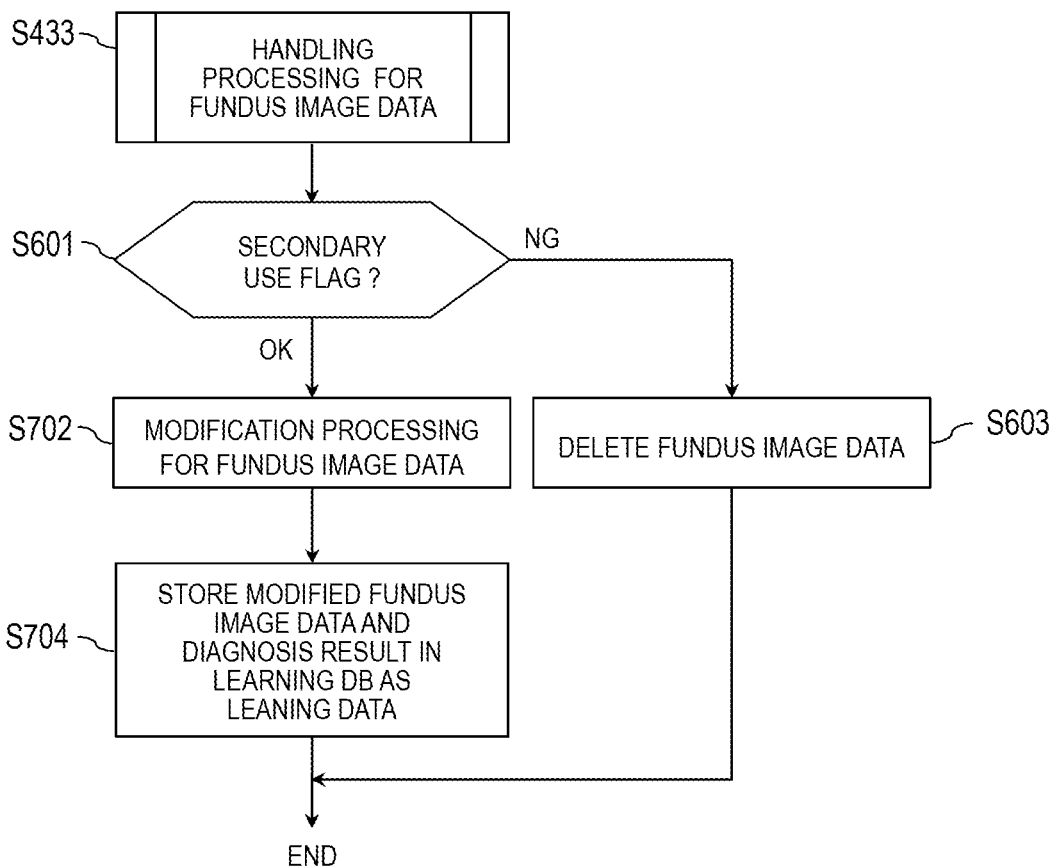
FIG. 7 is a flowchart illustrating a detailed example of a second processing procedure of the handling processing (Step S433) for the fundus image data illustrated in FIG. 4.

FIG. 7 is a flowchart illustrating a detailed example of a second processing procedure of the handling processing (Step S433) for the fundus image data 102 illustrated in FIG. 4. In FIG. 6, if the secondary use flag is OK, the fundus image data 102 and the diagnosis result Rij are stored in the learning DB 131 as the learning data without change. However, in FIG. 7, even when the secondary use flag is OK, the AI server 130 modifies the fundus image data 102 and then stores the fundus image data 102 in the learning DB 131 as the learning data in consideration of protecting personal information. The same steps as in FIG. 6 will be given the same step numbers and descriptions thereof will be omitted.

When the secondary use flag, which is the second agreement information 103b, is "1" indicating permission (OK) for secondary use (Step S601: Yes), the AI server 130 performs modification processing for the fundus image data 102 (Step S702). An example of the modification processing (Step S702) for the fundus image data 102 will now be described. The modification processing (Step S702) is image processing for preventing the fundus image data from being illegally used if the fundus image data leaks. For example, the modification processing is processing that aims to prevent illegal access to a retina authentication system using the fundus image data or illegal registration to a fundus image data database.

Figure 8:
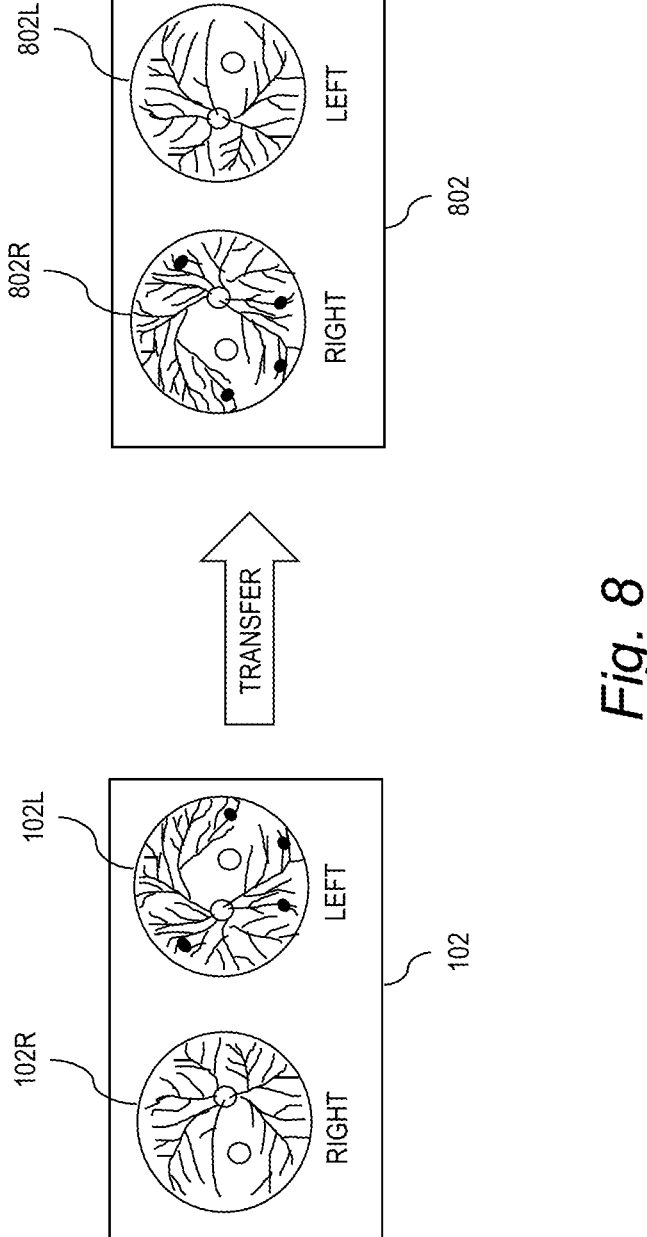
FIG. 8 is a diagram illustrating a first example of modification processing (Step S702) for the fundus image data.

FIG. 8 is a diagram illustrating a first example of modification processing (Step S702) for the fundus image data 102. In FIG. 8, the AI server 130 inverts and transfers the right-eye fundus image data 102R into a new left-eye fundus image data 802L, and inverts and transfers the left-eye fundus image data 102L into a new right-eye fundus image data 802R. In this case, the AI server 130 also changes a diagnosis result RijR into a diagnosis result RijL and a diagnosis result RijL into a diagnosis result RijR.

Figure 9:
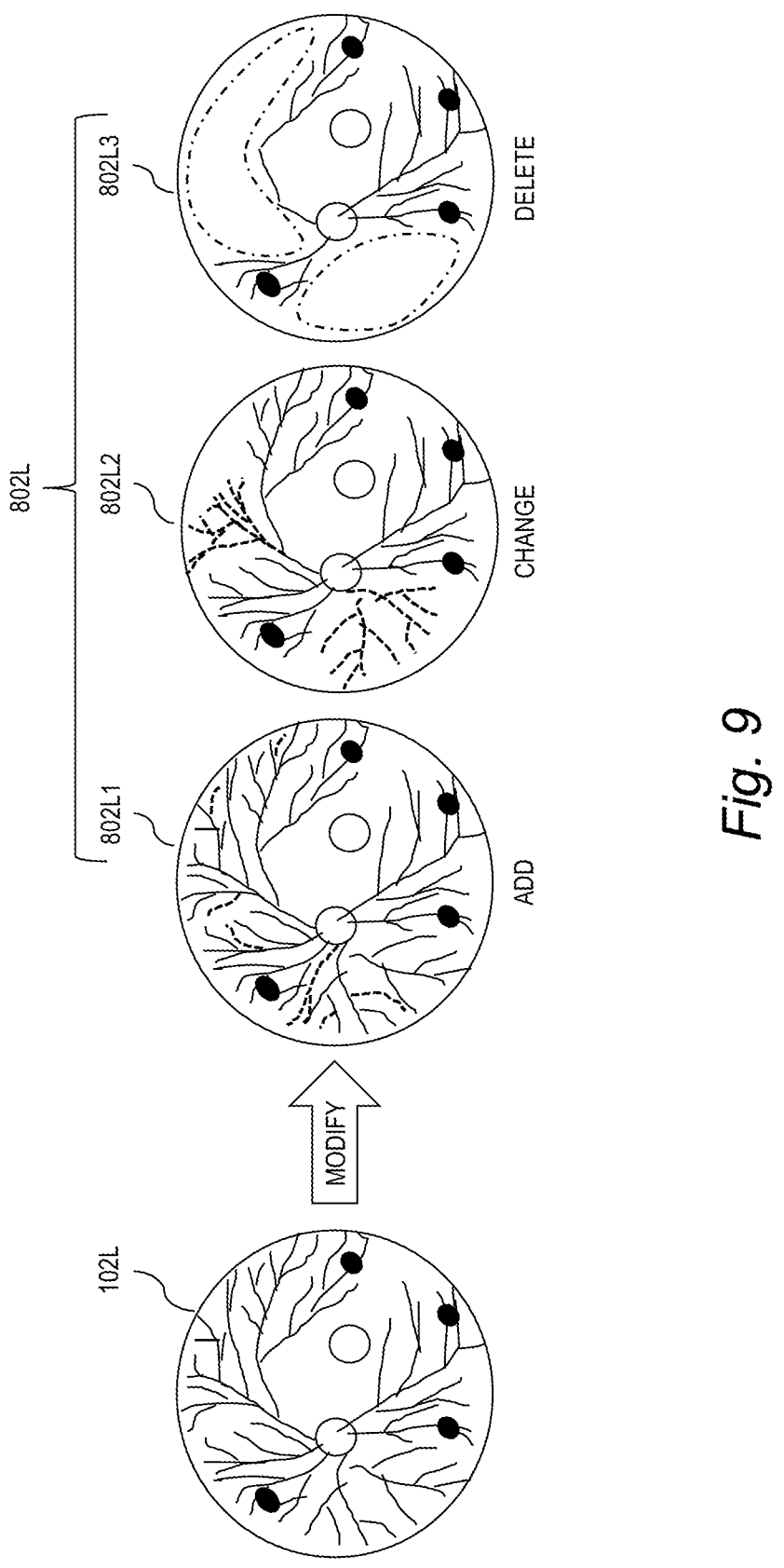
FIG. 9 is a diagram illustrating a second example of modification processing (Step S702) for the fundus image data.

FIG. 9 is a diagram illustrating a second example of modification processing (Step S702) for the fundus image data 102. FIG. 9 illustrates a modifying example of the fundus image data 102 for the left eye, but the fundus image data 102 for the right eye may be modified in the same way. The AI server 130 can add blood vessel shape data to the fundus image data 102L to modify the fundus image data 102L and create a fundus image data 102L1.

The AI server 130 can also modify the fundus image data 102L to create a fundus image data 102L2 by altering paths of the blood vessel shape data in the fundus image data 102L. Further, the AI server 130 can modify the fundus image data 102L to create a fundus image data 102L3 by deleting the blood vessel shape data from the fundus image data 102L. When adding, altering or deleting the blood vessel data, the diagnosis result Rij cannot be replaced, unlike in left-right inversion.

When adding, altering and deleting as illustrated in FIG. 9, the AI server 130 preferably references the diagnosis result Rij to modify image data within a healthy region not associated with an abnormal region in the fundus image data 102L. A "healthy region" refers to, for example, a region where a microaneurysm is not present in a case where the diagnosis result Rij indicates mild non-proliferative retinopathy (Mild. Hereinafter, "first retinopathy"), a region where an avascular field is not present in a case where the diagnosis result Rij indicates moderate or severe non-proliferative retinopathy (Moderate or Severe. Hereinafter, "second retinopathy"), or a region where no neovascularity has been detected in a case where the diagnosis result Rij indicates proliferative retinopathy (Proliferative. Hereinafter, "third retinopathy"). Modifying the healthy region does not affect the diagnosis result Rij. With this configuration, the diagnosis result before the modification can be maintained after the fundus image data 102 is modified.

Figure 10:
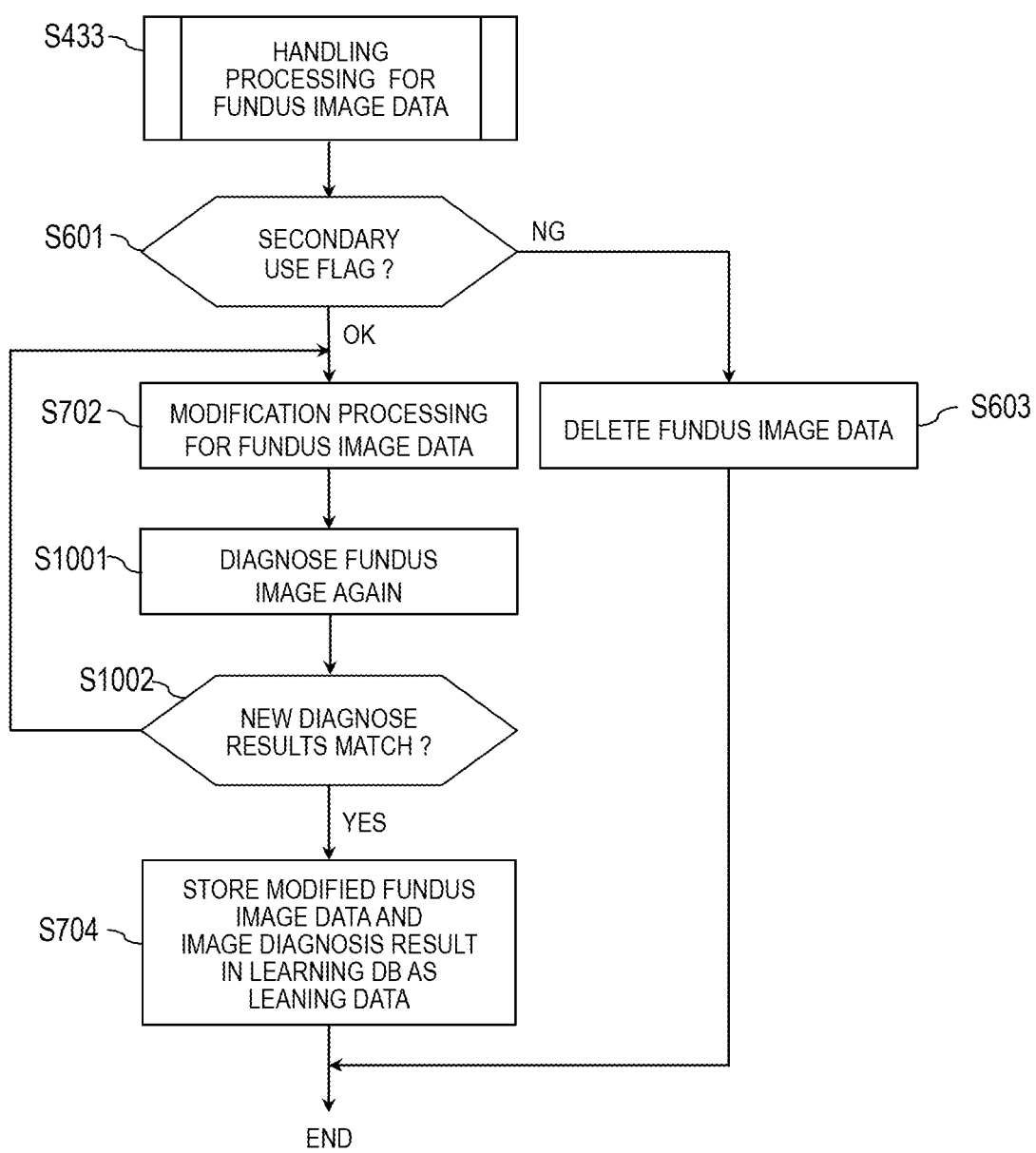
FIG. 10 is a flowchart illustrating a third detailed processing procedure of the handling processing (Step S433) for the fundus image data 102 illustrated in FIG. 4.

By modifying the fundus image data 102 as illustrated in FIGS. 9 and 10, illegal use for retina authentication can be prevented even if the modified fundus image data 802 leaks. Thus, this modify can disable retina authentication and increase security. Security may be further increased by encrypting the fundus image in addition to modifying the fundus image data 102.

Returning to FIG. 7, the AI server 130 stores a combination of the fundus image data 802 modified in Step S702 and the diagnosis result Rij in the learning DB 131 as learning data (Step S704) and ends the handling processing for the fundus image data 102 (Step S433). As a result, the modified fundus image data 802 can be used again while taking the privacy of the patient i into consideration.

FIG. 10 is a flowchart illustrating a third detailed processing procedure of the handling processing (Step S433) for the fundus image data 102 illustrated in FIG. 4. FIGS. 7 to 9 illustrate examples where the fundus image data 102 is modified. However, a diagnosis result Rij different to the diagnosis result Rij before the modification may be obtained depending on the degree of modification.

Thus, in FIG. 10, the AI server 130 conducts fundus image diagnosis again for the modified fundus image data 802 and, if the diagnosis result Rij is the same as the diagnosis result Rij before the modification, the AI server 130 stores the fundus image data 802 in the learning DB 131 as learning data for secondary use. Thus, personal information can be protected and the same diagnosis result can be obtained before and after the modification.

The same steps as in FIGS. 6 and 7 are given the same step numbers and descriptions thereof will be omitted. After the modification processing (Step S702) for the fundus image data 102 illustrated in FIG. 7, the AI server 130 repeats the fundus image diagnosis for the modified fundus image data 802 (Step S1001).

Then, the AI server 130 determines whether the repeated diagnosis result Rij obtained in Step S1001 and the diagnosis result Rij before change are the same (Step S1002). Specifically, for example, if the fundus image data 102 is inverted in Step S702 as illustrated in FIG. 8, the AI server 130 determines whether the repeated diagnosis result RijR for the right eye is the same as the diagnosis result RijL for the left eye before the modification, and determines whether the repeated diagnosis result RijL for the left eye is the same as the diagnosis result RijR for the right eye before the modification.

If, in Step S702, the fundus image data 102 is not inverted and the blood vessel shape data is added, altered or deleted as illustrated in FIG. 9, the AI server 130 determines whether the repeated diagnosis result RijR for the right eye is the same as the diagnosis result RijR for the right eye before the modification, and determines whether the repeated diagnosis result RijL for the left eye is the same as the diagnosis result RijL for the left eye before the modification.

If the two eyes do not match (Step S1002: No), the processing returns to Step S702 and the AI server 130 repeats the modification processing for the fundus image data 102 (Step S702). In this case, the AI server 130 performs modification different to the already performed modification, such as adding, altering or deleting blood vessel shape data. However, if the blood vessel shape data to be added, changed, or deleted is different from the already added, changed, or deleted blood vessel shape data, this is considered to be a different modification.

If the two eyes match (Step S1002: Yes), the AI server 130 stores a combination of the newest fundus image data 802 modified in Step S702 and the diagnosis result Rij in the learning DB 131 as learning data (Step S704) and ends the handling processing (Step S433) for the fundus image data 102.

Ensuring the same diagnosis result Rij before and after the modification makes it possible to reuse the modified fundus image data 802 having the same diagnosis result Rij while preventing illegal use of the fundus image data of the patient i and protecting the privacy of the patient i. Further, when the combination of the modified fundus image data 802 and the diagnosis result Rij is used as learning data, it is possible to prevent a reduction in prediction accuracy with the learning model used for fundus image diagnosis by the AI server 130.

Figure 11:
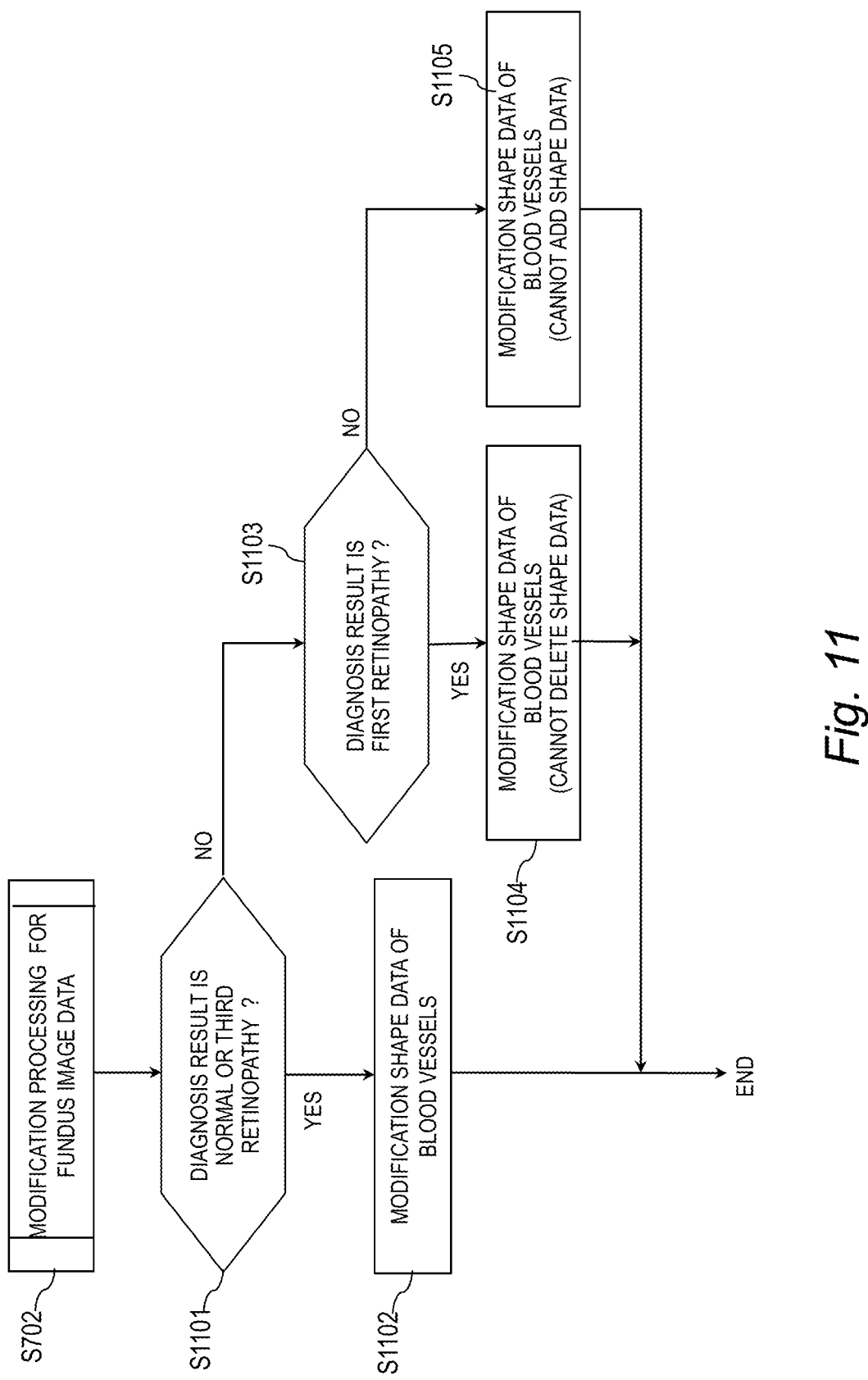
FIG. 11 is a flowchart illustrating a detailed example of another processing procedure of the fundus image data modification processing (Step S702) illustrated in FIGS. 7 and 9.
Figure 12:
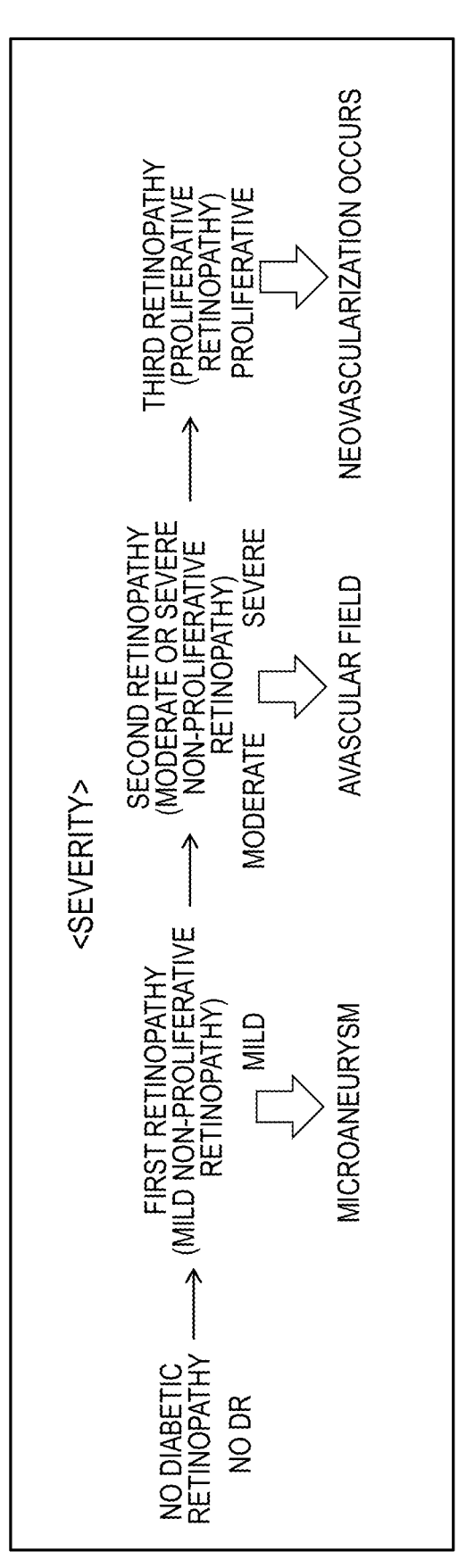
FIG. 12 is a diagram illustrating an example of severity of a diabetic retinopathy.

FIG. 11 is a flowchart illustrating a detailed example of another processing procedure of the fundus image data modification processing (Step S702) illustrated in FIGS. 7 and 9. FIG. 11 illustrates an example of a processing procedure in which the AI server 130 modifies blood vessel shape data in a retina based on severity, which is the diagnosis result Rij. FIG. 12 is a diagram illustrating an example of severity of a diabetic retinopathy.

In FIG. 11, the AI server 130 determines whether the diagnosis result Rij is normal (No DR) (Step S1101). If the diagnosis result Rij is normal (No DR) (Step S1101: Yes), the AI server 130 modifies the blood vessel shape data in the fundus image data 102 as illustrated in FIG. 8 or 9 (Step S1102). Then, the AI server 130 ends the fundus image data modification processing (Step S702) and moves to the next processing.

If the diagnosis result Rij is not normal (No DR) (Step S1101: No), the AI server 130 determines whether the diagnosis result Rij indicates the first retinopathy (Mild) or the third retinopathy (Proliferative) (Step S1103). If the diagnosis result Rij indicates the first retinopathy (Mild) or the third retinopathy (Proliferative) (Step S1103: Yes), the AI server 130 modifies the blood vessel shape data in the fundus image data 102 as illustrated in FIG. 8 or 9 (Step S1104).

In the first retinopathy (Mild), a microaneurysm occurs. In the third retinopathy (Proliferative), neovascularity occurs. Thus, in order to prevent shape data of a microaneurysm or neovascularity from being deleted, shape data in the modification in Step S1104 can be added or altered but not deleted. Then, the AI server 130 ends the fundus image data modification processing (Step S702) and moves to the next processing.

If the diagnosis result Rij is not the first retinopathy (Mild) or the third retinopathy (Proliferative) (Step S1103: No), the diagnosis result Rij corresponds to the second retinopathy (Moderate or Severe). Thus, the AI server 130 modifies the blood vessel shape data in the fundus image data 102 as illustrated in FIG. 8 or 9 (Step S1105).

In the second retinopathy (Moderate or Severe), an avascular field is present in a predetermined range. Thus, in order to prevent blood vessel shape data from being added to the avascular field, shape data in the modification in Step S1105 can be altered or deleted but not added. Even if blood vessel shape data is added to the avascular field through alteration, such modification corresponds to adding shape data and is thus disallowed. Then, the AI server 130 ends the fundus image data modification processing (Step S702) and moves to the next processing.

Through the AI server 130 modifying the shape data indicating tissue of the eye according to the diagnosis result Rij, it is possible to prevent the diagnosis result Rij from being changed before and after the modification. Ensuring the same diagnosis result Rij before and after the modification makes it possible to reuse the modified fundus image data 802 for which the diagnosis result Rij has not changed, while preventing illegal use of the fundus image data of the patient i and protecting the privacy of the patient i. Further, when the combination of the modified fundus image data 802 and the diagnosis result Rij is used as learning data, it is possible to prevent a reduction in prediction accuracy with the learning model used for fundus image diagnosis by the AI server 130.

Example of Functional Configuration of Information Processing System

Figure 13:
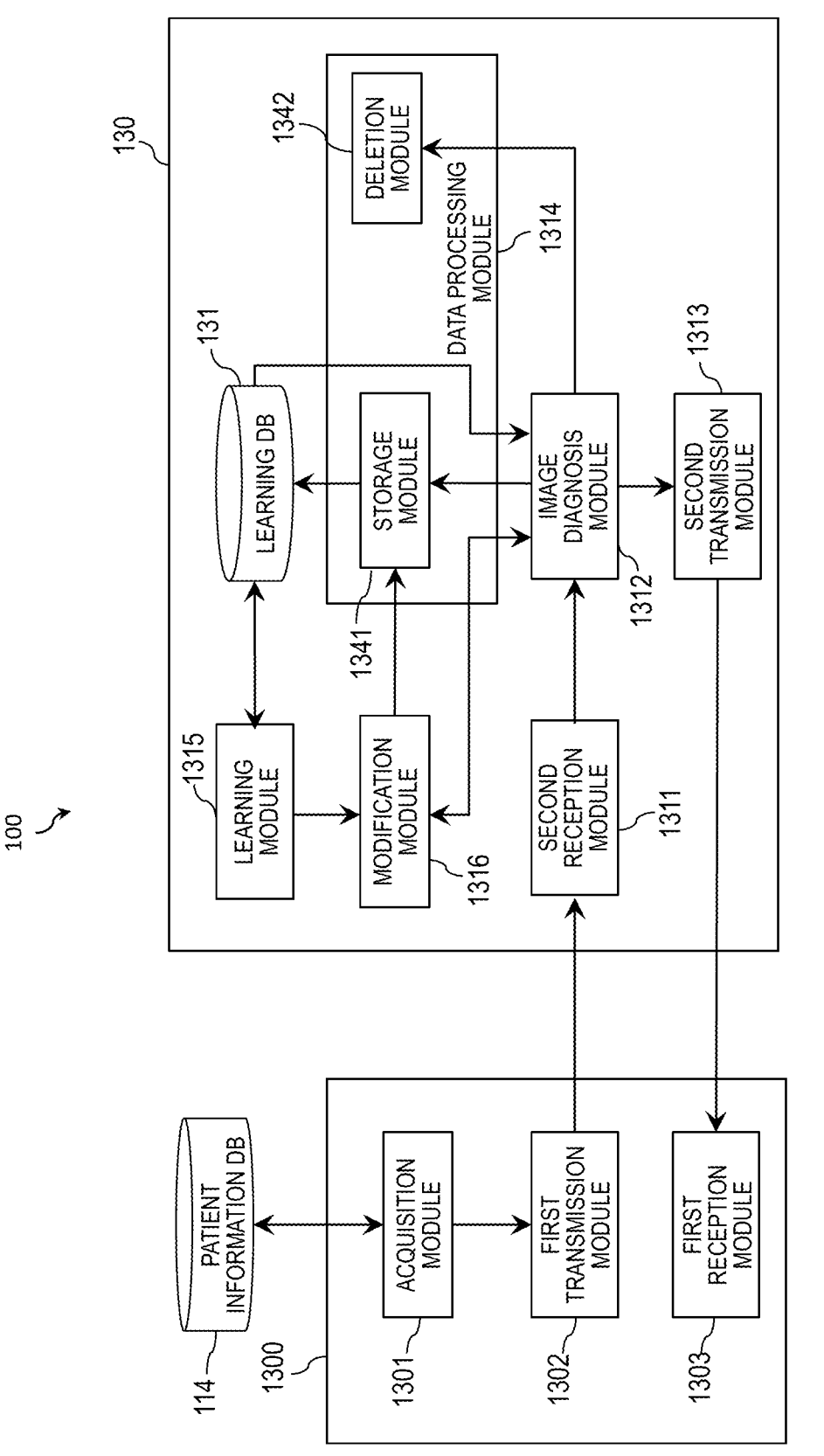
FIG. 13 is a block diagram illustrating an example of the functional configuration of the information processing system according to the first embodiment.

FIG. 13 is a block diagram illustrating an example of the functional configuration of the information processing system according to the first embodiment. In FIG. 13, an information processing apparatus 1300 is a computer including the image acquisition apparatus 400 (terminal 112 and hospital server 113) and the management server 120. The information processing apparatus 1300 includes an acquisition module 1301, a first transmission module 1302, and a first reception module 1303. Specifically, the acquisition module 1301, the first transmission module 1302 and the first reception module 1303 are realized by, for example, causing the processor 201 to run a program stored in the storage device 202 illustrated in FIG. 2.

The acquisition module 1301 acquires various types of data from the image acquisition apparatus 400. Specifically, for example, the acquisition module 1301 acquires the diagnosis information Dij and patient information related to the patient i in question from the patient information DB 114 from the image acquisition apparatus 400 as illustrated in Steps S411 to S413 in FIG. 4. The diagnosis information Dij includes the agreement information 103. The acquisition module 1301 performs the anonymization processing for patient information as illustrated in Step S422 in FIG. 4 to acquire an anonymization ID as identification information unique to the fundus image data 102.

As illustrated in Steps S425 and S426 in FIG. 4, the acquisition module 1301 acquires the diagnosis result data 105 related to the patient i based on the patient information identified from the anonymization ID included in the anonymous diagnosis result data 107 output from the AI server 130 and the diagnosis result Rij included in the anonymous diagnosis result data 107, and stores the diagnosis result data 105 in the management server 120.

The first transmission module 1302 transmits various types of data using the image acquisition apparatus 400. Specifically, for example, if the first agreement information 103a indicates permission for transmitting, the first transmission module 1302 uses the image acquisition apparatus 400 to transmit the diagnostic data 104 including the patient information related to the patient i, the fundus image data 102 and the second agreement information 103b to the management server 120 as illustrated in Step S415 in FIG. 4. As illustrated in Step S423 in FIG. 4, the first transmission module 1302 uses the management server 120 to transmit the anonymous diagnostic data 106 including the anonymization ID, the fundus image data 102 and the second agreement information 103b to the AI server 130.

The first reception module 1303 receives various types of data using the image acquisition apparatus 400. Specifically, for example, the first reception module 1303 receives the anonymous diagnosis result data 107 from the AI server 130 as illustrated in Step S424 in FIG. 4. Further, the first reception module 1303 receives the completion information indicating that reception of the anonymous diagnosis result data 107 in Step S424 is complete using the image acquisition apparatus 400. The first reception module 1303 also receives the diagnosis result data 105 from the management server 120 using the image acquisition apparatus 400.

The AI server 130 includes a second reception module 1311, an image diagnosis module 1312, a second transmission module 1313, a data processing module 1314, a learning module 1315, a modification module 1316, and the learning DB 131. Specifically, the second reception module 1311, the image diagnosis module 1312, the second transmission module 1313, the data processing module 1314, the learning module 1315, and the modification module 1316 are realized by, for example, causing the processor 201 to run a program stored in the storage device 202 illustrated in FIG. 2. The learning DB 131 is specifically realized by, for example the storage device 202 illustrated in FIG. 2.

As illustrated in Step S431 in FIG. 4, the second reception module 1311 receives the anonymous diagnostic data 106 transmitted from the first transmission module 1302 in the information processing apparatus 1300.

As illustrated in Step S432 in FIG. 4, the image diagnosis module 1312 inputs the fundus image data to the learning model in which updated learning parameters have been applied to the CNN, performs fundus image diagnosis, and outputs severity as the diagnosis result Rij to the second transmission module 1313.

As illustrated in Step S434 in FIG. 4, machine learning or deep learning, more specifically, for example, the second transmission module 1313 transmits the anonymous diagnosis result data including the diagnosis result Rij to the first reception module 1303 in the information processing apparatus 1300.

As illustrated in Step S433 in FIG. 4, the data processing module 1314 performs the handling processing for the fundus image data in FIGS. 7 and 10. Specifically, for example, the data processing module 1314 includes a storage module 1341 and a deletion module 1342. If the secondary use flag is OK, the storage module 1341 stores the learning data, which is a combination of the fundus image data 102 diagnosed by the image diagnosis module 1312, and the diagnosis result Rij and, if the secondary use flag is NG, the deletion module 1342 deletes the fundus image data 102 diagnosed by the image diagnosis module 1312.

The learning module 1315 generates the learning model by providing the CNN with the learning dataset in the learning DB 131 and updating the learning parameters in the CNN.

As illustrated in Step S702 in FIGS. 7 and 10, the modification module 1316 modifies the fundus image data 102 diagnosed by the image diagnosis module 1312. In this case, if the secondary use flag is OK, the storage module 1341 stores learning data that is a combination of the modified fundus image data 802 modified by the modification module 1316 and the diagnosis result Rij. Further, the modification module 1316 acquires the diagnosis result Rij for the modified fundus image data 802 by using the learning module 1315 to input the modified fundus image data 802 to the newest learning model. In this case, the modification module 1316 may modify the fundus image data 102 until the diagnosis results Rij before and after the modification match.

As described above, in the first embodiment, ensuring the same diagnosis result Rij before and after the modification makes it possible to reuse the modified fundus image data 802 for which the diagnosis result Rij has not changed, while protecting the privacy of the patient i. Further, when the combination of the modified fundus image data 802 and the diagnosis result Rij is used as learning data, it is possible to prevent a reduction in prediction accuracy with the learning model used for fundus image diagnosis by the AI server 130.

Note that for a first-time image diagnosis for a patient i, the image acquisition apparatus 400 generates the first agreement information 103a and the second agreement information 103b and, for a second or subsequent image diagnosis for a patient i, the first agreement information 103a and the second agreement information 103b generated for the first time may be used. With this configuration, there is no need to reconfigure the agreement information 103 and convenience can be improved.

Alternatively, for a first-time image diagnosis for a patient i, the image acquisition apparatus 400 generates the first agreement information 103a and the second agreement information 103b and, for a second or subsequent image diagnosis for a patient i, the image acquisition apparatus 400 may use the first agreement information 103a generated for the first time and output an update request for the second agreement information 103b. The update request is, for example, displayed on a display screen of the terminal 112. When the update request is displayed on the display screen, the patient i or a physician sets the secondary use flag, which is the second agreement information 103b, to "1" (OK) or "0" (NG). After the secondary use flag is set, the hospital server 113 refers to the first agreement information 103a and determines whether to transmit the secondary use flag to the management server 120. If transmitting the secondary use flag, the diagnostic data 104 is transmitted to the management server 120.

With this configuration, there is no need to reconfigure the first agreement information 103a, convenience can be improved, and privacy protection can be improved by urging the patient i to check the second agreement information 103b.

Second Embodiment

Next, a second embodiment will be described. In the first embodiment, the AI server 130 included the learning DB 131. However, the second embodiment will deal with an example where the AI server 130 and the learning DB 131 are separate. The learning DB 131 includes a DB server 1400 that is different to the AI server 130. The management server 120 may perform the function of the DB server 1400. Note that the second embodiment will primarily focus on differences to the first embodiment. Components similar to those in the first embodiment will be given the same reference symbols and descriptions will be omitted.

Figure 14:
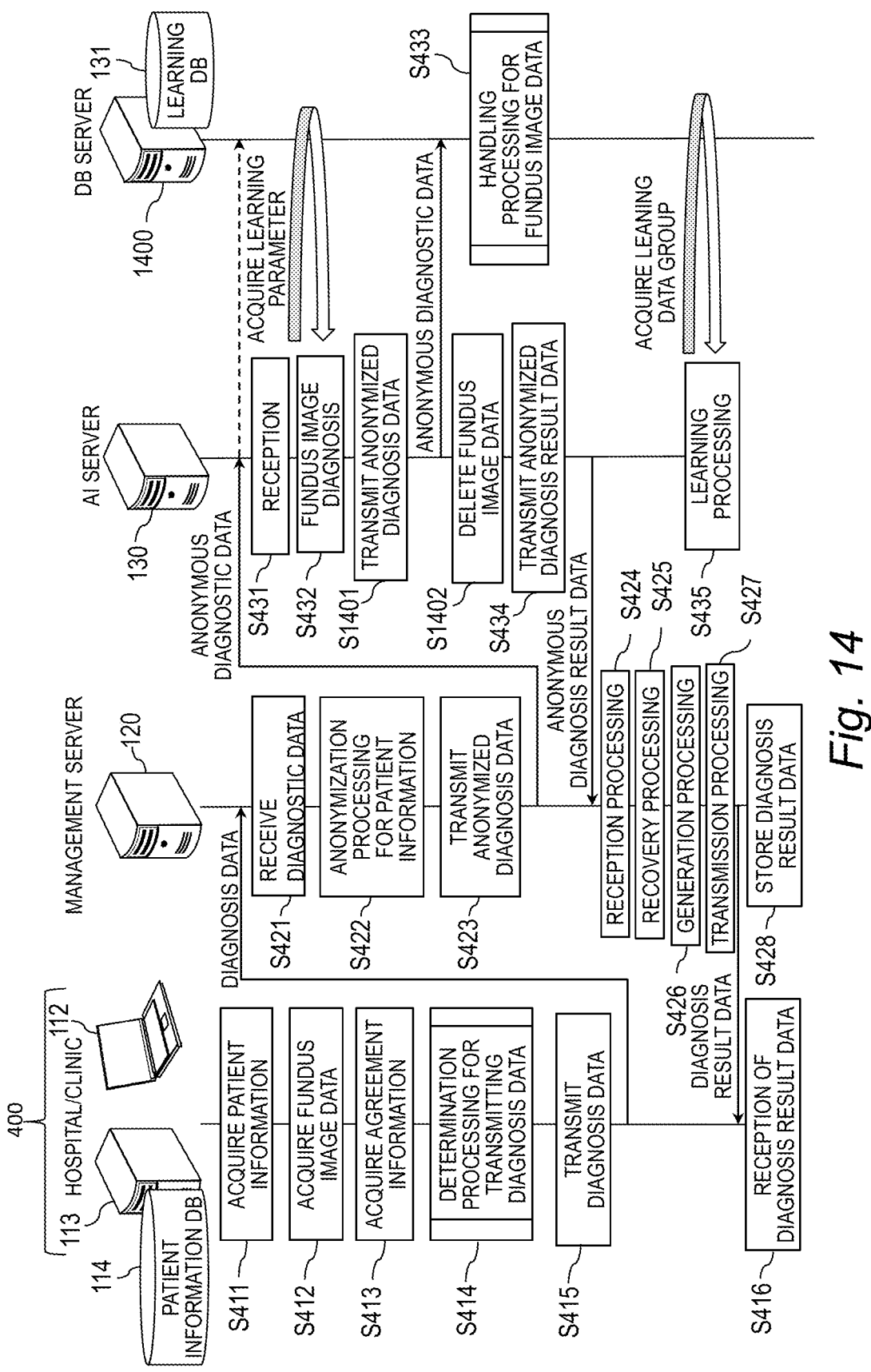
FIG. 14 is a diagram illustrating an example of an operation sequence of the information processing system according to a second embodiment.

FIG. 14 is a diagram illustrating an example of an operation sequence of the information processing system 100 according to a second embodiment. The AI server 130 acquires the learning parameters from the DB server 1400 and performs fundus image diagnosis (Step S1432). Step S1432 is different to Step S432 in that the learning parameters are acquired from the DB server 1400.

After performing fundus image diagnosis (Step S1432), the AI server 130 transmits the anonymous diagnostic data 106 to the DB server 1400 (Step S1401). In this case, the DB server 1400 performs the handling processing for the fundus image data 102 (Step S1433). In order to prevent data leakage, the AI server 130 deletes the fundus image data 102 (Step S1402). Then, the AI server 130 acquires the learning dataset from the learning DB 131 and performs learning processing (Step S1434). The Step S1434 is different to Step S434 in that the learning dataset is acquired from the DB server 1400. Then, the AI server 130 ends the processing in the received fundus image and stands by to receive the next fundus image.

Figure 15:
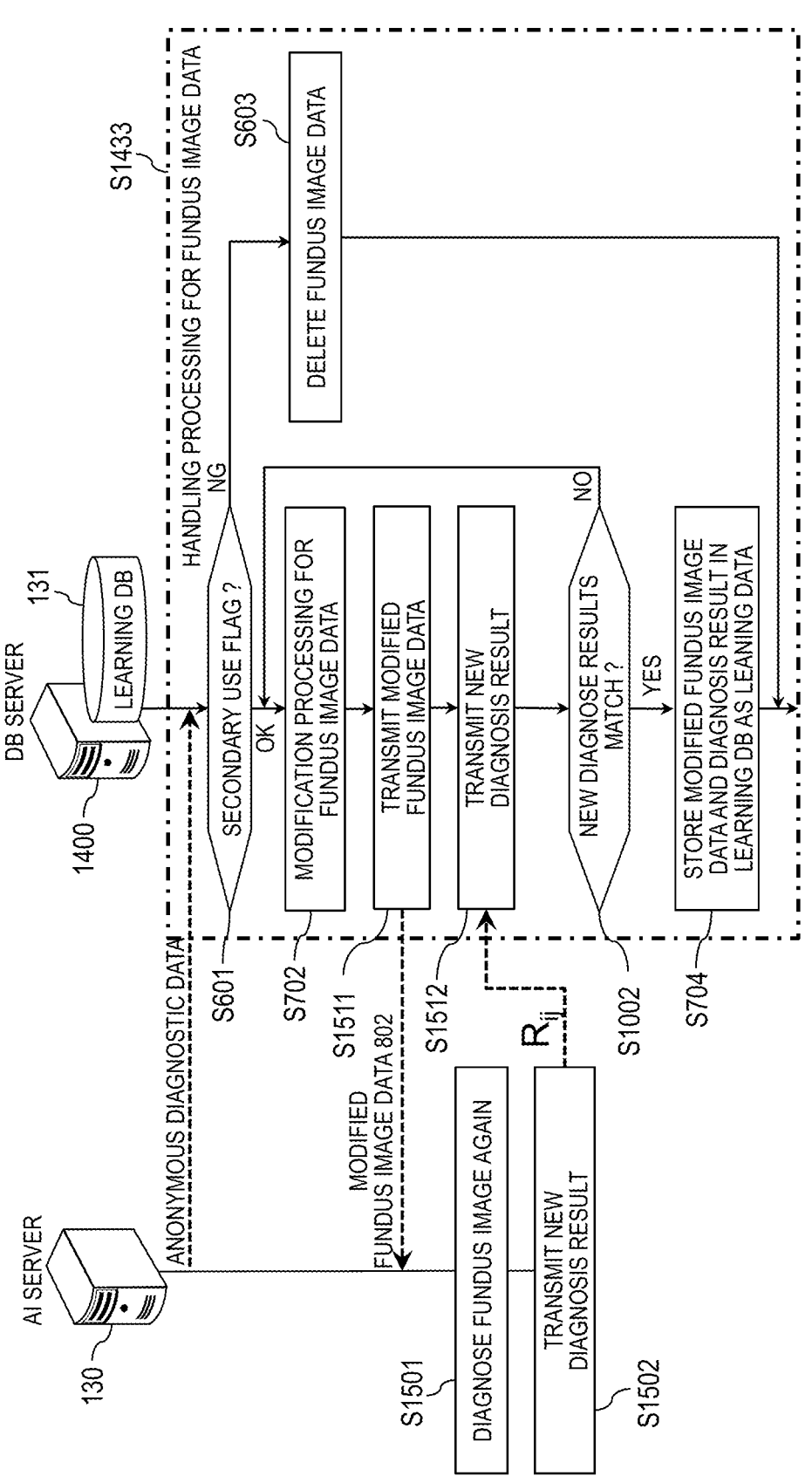
FIG. 15 is a diagram illustrating an example of a detailed operation sequence of the handling processing (Step S432) for the fundus image data illustrated in FIG. 14.

FIG. 15 is a diagram illustrating an example of a detailed operation sequence of the handling processing (Step S432) for the fundus image data 102 illustrated in FIG. 14. When the DB server 1400 receives the anonymous diagnostic data 106, if the secondary use flag, which is the second agreement information 103b, is "0" indicating non-permission (NG) for secondary use, the DB server 1400 deletes the fundus image data 102 and ends the handling processing (Step S1433) for the fundus image data 102.

If the secondary use flag, which is the second agreement information 103b, is "1" indicating permission (OK) for secondary use (Step S601: Yes), the DB server 1400 performs modification processing for the fundus image data 102 (Step S702). Then, the DB server 1400 transmits the modified fundus image data 802 to the AI server 130 (Step S1511).

When the AI server 130 receives the modified fundus image data 802 from the DB server 1400, the AI server 130 inputs the modified fundus image data 802 to the learning model and repeats the fundus image diagnosis (Step S1501). Then, the AI server 130 transmits the repeated diagnosis result Rij to the DB server 1400 (Step S1502).

The DB server 1400 receives the repeated diagnosis result Rij from the AI server 130 (Step S1512). Then, the DB server 1400 determines whether the repeated diagnosis result Rij and the diagnosis result Rij of the fundus image data 102 before the modification are the same (Step S1002). If the results are not the same (Step S1002: No), the processing returns to Step S702 and the DB server 1400 modifies the fundus image data 102 again (Step S702). If the results are the same (Step S1002: Yes), the DB server 1400 stores the modified fundus image data 802 and the repeated diagnosis result Rij as the learning model in the learning DB 131 (Step S704). Then, the handling processing (Step S1433) for the fundus image data 102 ends.

Example of Functional Configuration of Information Processing System

Figure 16:
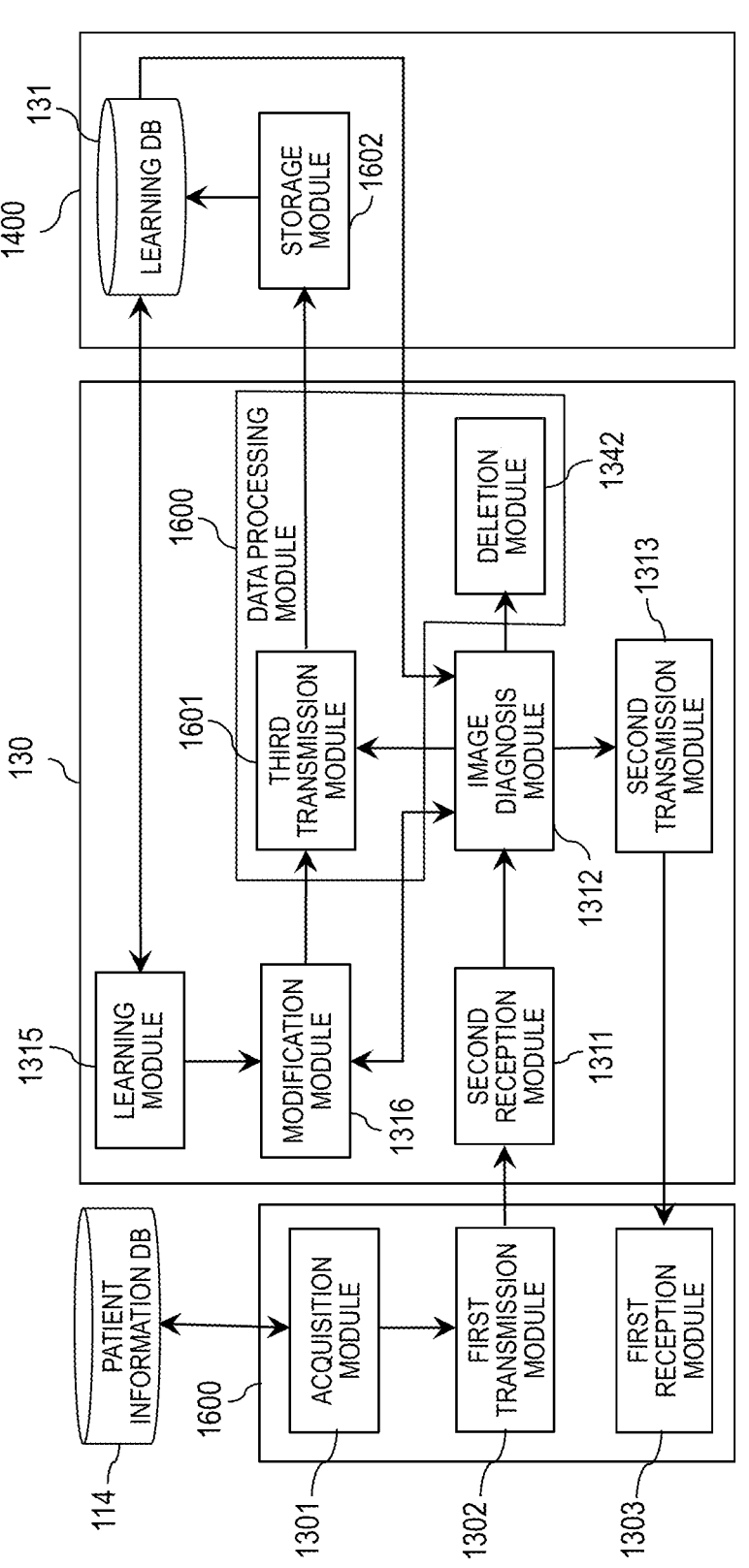
FIG. 16 is a block diagram illustrating an example of the functional configuration of the information processing system according to the second embodiment.

FIG. 16 is a block diagram illustrating an example of the functional configuration of the information processing system according to the second embodiment. In FIG. 16, the data processing module 1600 of the AI server 130 includes the deletion module 1342 and the third transmission module 1601, and the DB server 1400 includes the learning DB 131 and the storage module 1602. If the secondary use flag is OK, the third transmission module 1601 transmits the modified fundus image data 802 and the diagnosis result Rij to the DB server 1400. The storage module 1602 stores the modified fundus image data 802 and the diagnosis result Rij from the third transmission module 1601 in a learning dataset in the learning DB 131 as the learning data.

As described above, even in the second embodiment, ensuring the same diagnosis result Rij before and after the modification makes it possible to reuse the modified fundus image data 802 for which the diagnosis result Rij has not changed, while protecting the privacy of the patient i. Further, when the combination of the modified fundus image data 802 and the diagnosis result Rij is used as learning data, it is possible to prevent a reduction in prediction accuracy with the learning model used for fundus image diagnosis by the AI server 130.

Note that the present invention is not limited to the above-described embodiments and the embodiments may be combined as desired. Further, other aspects may be included in the scope of the present invention within a range not departing from the technical gist of the present invention.

EXPLANATION OF SYMBOLS

100 information processing system, 101 hospital system, 102 fundus image data, 103 agreement information, 103*a* first agreement information, 103*b* second agreement information, 104 diagnosis data, 105 diagnosis result data, 106 anonymous diagnostic data, 107 anonymous diagnostic result data, 111 ophthalmological device, 112 terminal, 113 hospital server, 114 patient information DB, 120 management server, 130 AI server, 131 learning DB, 201 processor, 202 storage device, 400 image acquisition apparatus, 802 modified fundus image data, 1300 information processing apparatus, 1301 acquisition module, 1302 first transmission module, 1303 first reception module, 1311 second reception module, 1312 image diagnosis module, 1313 second transmission module, 1314 data control module, 1315 learning module, 1316 modification module, 1341 storage module, 1342 deletion module, 1400 DB server, 1601 third transmission module, 1602 storage module, Dij diagnosis information, Rij diagnosis result

What is claimed is:

1. An information processing system including an image acquisition apparatus configured to acquire subject eye image data of a patient, a first information processing apparatus which is communicably connected with the image acquisition apparatus and stores the subject eye image data, and a second information processing apparatus which is communicably connected with the first information processing apparatus and performs image diagnosis using the subject eye image data, wherein the image acquisition apparatus is configured to execute:

first generation processing of generating first agreement information indicating permission or non-permission from the patient for transmitting the subject eye image data to the first information processing apparatus, and second agreement information indicating permission or non-permission from the patient for reusing the subject eye image data by the second information processing apparatus for after image diagnosis with the second information processing apparatus; and first transmission processing of, when the first agreement information indicates transmission permission, transmitting first transmission data including patient information of the patient, the subject eye image data and the second agreement information to the first information processing apparatus, wherein the first information processing apparatus is configured to execute:

storage processing of storing the subject eye image data when the first transmission data is received from the image acquisition apparatus;

second generation processing of generating identification information unique to the subject eye image data when the first transmission data is received; and second transmission processing of transmitting second transmission data including the identification information, the subject eye image data, and the second agreement information to the second information processing apparatus, wherein the second information processing apparatus is configured to execute:

image diagnosis processing of executing image diagnosis on the basis of the subject eye image data when the second transmission data is received from the first information processing apparatus;

data processing of deleting the subject eye image data after the image diagnosis processing when the second agreement information indicates non-permission for reusing the subject eye image data, and storing the subject eye image data and an image diagnosis result of the image diagnosis processing in a database when the second agreement information indicates permission for reuse of the subject eye image data; and third transmission processing of transmitting third transmission data including the identification information and the image diagnosis result to the first information processing apparatus.

2. The information processing system according to claim 1, wherein the first information processing apparatus is configured to execute:

third generation processing of generating diagnosis result data of the patient on the basis of the patient information identified from the identification information included in the third transmission data transmitted by the third transmission processing and the diagnosis results included in the third transmission data; and second storage processing of storing the diagnosis result data with the subject eye image data identified from the identification information.

3. The information processing system according to claim 2, wherein the image acquisition apparatus is configured to execute fifth transmission processing of transmitting an acquisition request for the diagnosis result data to the first information processing apparatus, and wherein the first information processing apparatus is configured to execute sixth transmission processing of transmitting the diagnosis result data to the image acquisition apparatus when the acquisition request is received.

4. The information processing system according to claim 1, wherein the first information processing apparatus is configured to execute fourth transmission processing of, when the third transmission data is received, transmitting completion information indicating that image diagnosis of the subject eye image data identified from the identification information is complete.

5. The information processing system according to claim 1, wherein the second information processing apparatus is configured to execute learning processing of performing machine learning using the subject eye image data and the image diagnosis result stored in the database to generate a learning parameter, and wherein, in the image diagnosis processing, the second information processing apparatus uses the learning parameter generated by the learning processing to execute the image diagnosis on the subject eye image data.

6. The information processing system according to claim 1, wherein the subject eye image data is at least one of or a combination of two or more of fundus image data obtained by a fundus camera, fundus image data obtained by a scanning laser ophthalmoscope, and tomographic data obtained by optical coherence tomography.

7. The information processing system according to claim 1, wherein, in the image diagnosis processing, the second information processing apparatus diagnoses a lesion in an eye using the subject eye image data.

8. The information processing system according to claim 1, wherein, in the image diagnosis processing, the second information processing apparatus diagnoses diabetic retinopathy using the subject eye image data.

9. The information processing system according to claim 1, wherein the second information processing apparatus is configured to execute invalidation processing of invalidating retina authentication using the subject eye image data when the subject eye image data is stored in the database.

10. The information processing system according to claim 9, wherein, in the invalidation processing, the second information processing apparatus embeds data for invalidating the retina authentication into the subject eye image data.

11. The information processing system according to claim 9, wherein, in the invalidation processing, the second information processing apparatus inverts the left and right in the subject eye image data for both eyes.

12. The information processing system according to claim 1, wherein, in the first generation processing, if image diagnosis of the patient is executed for a first time, the image acquisition apparatus generates the first agreement information and the second agreement information and, if image diagnosis of the patient is executed for a second time subsequent to the first time, the image acquisition apparatus uses the first agreement information and the second agreement information generated at the first time.

13. The information processing system according to claim 1, wherein, in the first generation processing, if image diagnosis of the patient is executed for a first time, the image acquisition apparatus generates the first agreement information and the second agreement information and, if image diagnosis of the patient is executed for a second time subsequent to the first time, the image acquisition apparatus uses the first agreement information generated at the first time and outputs an update request for the second agreement information.

14. An information processing program for causing a processor in an information processing apparatus that is communicably connected with another first information processing apparatus which stores subject eye image data of a patient and another second information processing apparatus including a database which stores learning data to execute:

reception processing of receiving, from the first information processing apparatus, the subject eye image data and permission or non-agreement information from the patient for reuse of the subject eye image data by the information processing apparatus;

image diagnosis processing for performing image diagnosis on the basis of the subject eye image data received by the reception processing;

transmission processing of transmitting an image diagnosis result obtained by the image diagnosis processing to the other information processing apparatus; and data control processing of controlling to delete the subject eye image data or store the subject eye image data in the database on the basis of the permission or non-agreement information received by the reception processing.

15. An information processing method executed by an information processing apparatus that is communicably connected with another first information processing apparatus which stores subject eye image data of a patient and another second information processing apparatus including a database which stores learning data, the information processing method comprising:

reception processing of receiving, from the first information processing apparatus, the subject eye image data and non-permission or agreement information from the patient for reuse of the subject eye image data by the information processing apparatus;

image diagnosis processing of performing image diagnosis on the basis of the subject eye image data received by the reception processing;

transmission processing of transmitting an image diagnosis result obtained by the image diagnosis processing to the other first information processing apparatus; and data processing of deleting the subject eye image data or transmitting the subject eye image data to the other second information processing apparatus on the basis of the non-permission or agreement information received by the reception processing.

* * * * *